United States Patent
Garfield et al.

(10) Patent No.: US 10,328,254 B2
(45) Date of Patent: Jun. 25, 2019

(54) UTERINE ELECTRICAL STIMULATION SYSTEM AND METHOD

(71) Applicant: Dignity Health, San Francisco, CA (US)

(72) Inventors: Robert E. Garfield, Goodyear, AZ (US); Harvey Carp, Portland, OR (US); William L. Maner, Phoenix, AZ (US)

(73) Assignee: Dignity Health, San Francisco, CA (US)

( * ) Notice: Subject to any disclaimer, the term of this patent is extended or adjusted under 35 U.S.C. 154(b) by 226 days.

(21) Appl. No.: 15/334,059

(22) Filed: Oct. 25, 2016

(65) Prior Publication Data

US 2017/0036011 A1  Feb. 9, 2017

Related U.S. Application Data

(62) Division of application No. 14/609,093, filed on Jan. 29, 2015, now Pat. No. 9,572,972, which is a division
(Continued)

(51) Int. Cl.
*A61N 1/05* (2006.01)
*A61N 1/04* (2006.01)
(Continued)

(52) U.S. Cl.
CPC .......... *A61N 1/0521* (2013.01); *A61M 25/10* (2013.01); *A61N 1/0476* (2013.01); *A61N 1/05* (2013.01);
(Continued)

(58) Field of Classification Search
CPC ................ A61N 1/0476; A61N 1/0521; A61N 1/36007; A61N 1/0524
See application file for complete search history.

(56) References Cited

U.S. PATENT DOCUMENTS

| 3,589,370 A | 6/1971 | McDonald |
| 4,046,140 A | 9/1977 | Born |

(Continued)

FOREIGN PATENT DOCUMENTS

| WO | 9810831 A1 | 3/1998 |
| WO | 0056401 A1 | 9/2000 |

(Continued)

OTHER PUBLICATIONS

Bais, et al., Postpartum Haemorrhage in Nulliparous Women: Incidence and Risk Factors in Low and High Risk Women, A Dutch Population-Based Cohort Study on Standard (>500 ml) and Severe (>1000 ml) Postpartum Haemorrhage, European Journal of Obstetrics & Gynecology and Reproductive Biology, 2004, 115:166-172.
(Continued)

*Primary Examiner* — Michael W Kahelin
(74) *Attorney, Agent, or Firm* — Quarles & Brady LLP

(57) ABSTRACT

Systems and methods for applying stimulating current to a patient for treating insufficient uterine contractions are provided. The system includes stimulation electrodes of a balloon electrode array device, a ring electrode array device, an electrode probe device, or a mesh electrode array device. Some aspects of the invention also provide a connector and cable device for coupling the stimulation electrodes to electronics for generating and providing the stimulating current to the stimulation electrodes.

10 Claims, 20 Drawing Sheets

Related U.S. Application Data of application No. 13/881,812, filed as application No. PCT/US2011/057856 on Oct. 26, 2011, now Pat. No. 8,972,028.

(60) Provisional application No. 61/407,397, filed on Oct. 27, 2010.

(51) Int. Cl.
*A61N 1/36* (2006.01)
*A61M 25/10* (2013.01)

(52) U.S. Cl.
CPC ....... *A61N 1/0524* (2013.01); *A61N 1/36007* (2013.01); *A61M 2025/105* (2013.01)

(56) References Cited

U.S. PATENT DOCUMENTS

| | | | |
|---|---|---|---|
| 4,711,251 A | 12/1987 | Stokes | |
| 4,905,670 A | 3/1990 | Adair | |
| 5,000,177 A * | 3/1991 | Hoffmann | A61N 1/3752 607/2 |
| 5,026,368 A | 6/1991 | Adair | |
| 5,251,613 A | 10/1993 | Adair | |
| 5,443,470 A | 8/1995 | Stern et al. | |
| 5,671,736 A | 9/1997 | Pettit et al. | |
| 5,784,162 A | 7/1998 | Cabib et al. | |
| 5,791,346 A | 8/1998 | Craine et al. | |
| 5,846,238 A | 12/1998 | Jackson et al. | |
| 5,928,228 A * | 7/1999 | Kordis | A61B 5/0422 600/374 |
| 5,964,789 A | 10/1999 | Karsdon | |
| 5,989,184 A | 11/1999 | Blair | |
| 5,989,561 A | 11/1999 | Groenewegen | |
| 5,991,649 A | 11/1999 | Garfield et al. | |
| 6,039,701 A | 3/2000 | Sliwa et al. | |
| 6,151,527 A | 11/2000 | Boutos | |
| 6,246,901 B1 | 6/2001 | Benaron | |
| 6,356,777 B1 * | 3/2002 | Garfield | A61B 5/04882 600/372 |
| 6,421,553 B1 | 7/2002 | Costa et al. | |
| 6,485,413 B1 | 11/2002 | Boppart et al. | |
| 6,676,680 B1 | 1/2004 | Packer | |
| 6,694,192 B2 | 2/2004 | Policker et al. | |
| 6,719,686 B2 | 4/2004 | Coakley et al. | |
| 6,735,476 B2 | 5/2004 | Mellen | |
| 6,741,895 B1 | 5/2004 | Gafni et al. | |
| 6,879,858 B1 | 4/2005 | Adams | |
| 7,220,252 B2 | 5/2007 | Shah | |
| 7,231,260 B2 * | 6/2007 | Wallace | A61N 1/057 607/115 |
| 7,429,262 B2 | 9/2008 | Woloszko et al. | |
| 7,660,636 B2 | 2/2010 | Castel et al. | |
| 7,672,736 B2 | 3/2010 | Boling | |
| 2002/0183682 A1 | 12/2002 | Darvish et al. | |
| 2003/0055465 A1 | 3/2003 | Ben-Haim et al. | |
| 2003/0135245 A1 | 7/2003 | Campos | |
| 2004/0152970 A1 | 8/2004 | Hunter et al. | |
| 2005/0049509 A1 | 3/2005 | Mansour et al. | |
| 2006/0004353 A1 | 1/2006 | Koyfman et al. | |
| 2007/0055337 A1 | 3/2007 | Tanrisever | |
| 2007/0265532 A1 | 11/2007 | Maynard et al. | |
| 2008/0214931 A1 | 9/2008 | Dickfeld | |
| 2010/0016444 A1 | 1/2010 | Shi et al. | |
| 2011/0144468 A1 | 6/2011 | Boggs et al. | |

FOREIGN PATENT DOCUMENTS

| | | |
|---|---|---|
| WO | 2006121589 A2 | 11/2006 |
| WO | 2008121750 A2 | 10/2008 |
| WO | 2012058289 A2 | 5/2012 |

OTHER PUBLICATIONS

Cairns, et al., Stimulation Pulse Characteristics and Electrode Configuration Determine Site of Excitation in Isolated Mammalian Skeletal Muscle: Implications for Fatigue, J. Appl. Physiol., 2007, 103:359-368.

Catanzarite, et al., Respiratory Compromise After MgSO4 Therapy for Preterm Labor in a Woman with Myotonic Dystrophy, A Case Report, Journal of Reproductive Medicine, 2008, 53:220-222.

Chong, et al., Current Strategies for the Prevention of Postpartum Haemorrhage in the Third Stage of Labour, Current Opinion in Obstetrics and Gynecology, 2004, 16:143-150.

Cotter, et al., Prophylactic Oxytocin for the Third Stage of Labour (Review), The Cochrane Library, 2007, Issue 4, 73 pages.

Fawcus, et al., A Community-Based Investigation of Maternal Mortality From Obstetric Haemorrhage in Rural Zimbabwe, Tropical Doctor, 1997, 27:159-163.

Galuschky, et al., Dual-Chamber Cardiac Pacemaker Tester, Med. Biol. Eng. Comput., 1998, 36:233-237.

Gordon, et al., Muscle Atrophy and Procedures for Training After Spinal Cord Injury, Physical Therapy, 1994, 74 (1):50-60.

Gould, et al., Robotic Implantation of Gastric Electrical Stimulation Electrodes for Gastroparesis, Surg. Endosc., 2009, 23:508-512.

Gregory, et al., Impact of Varying Pulse Frequency and Duration on Muscle Torque Production and Fatigue, Muscle Nerve, 2007, 35:504-509.

Hayashi, et al., Chapter 11, Obstetric Hemorrhage and Puerperal Sepsis, Essentials of Obstetrics and Gynecology, Fourth Edition, Copyright 2004, Elsevier Inc., 18 pages.

Hollingsworth, Mechanical Responses of Rat Isolated Uterine Horns to Transmural Stimulation, Br. J. Pharmac., 1975, 55:41-46.

Hughes, et al., Relaxin as a Relaxant of the Isolated Rat Uterus: Comparison With Its Mechanism of Action In Vivo, Gen. Pharmac., 1997, 29(5):829-833.

Lucas, et al., What Is the Ideal Pulse Frequency for Skeletal Muscle Stimulation After Cardiomyoplasty?, PACE, 1991, Part 1, 14:778-782.

Marzioni, et al., Restricted Innervation of Uterus and Placenta During Pregnancy: Evidence for a Role of the Repelling Signal Semaphorin 3A, Developmental Dynamics, 2004, 231:839-848.

Molloy, et al., Delivery After Caesarean Section: Review of 2176 Consecutive Cases, British Medical Journal, 1987, 294:1645-1647.

Morizaki, et al., A Functional and Structural Study of the Innervation of the Human Uterus, Am. J. Obstet. Gynecol., 1989, 160:218-228.

Morone, et al., The Use of Electrical Stimulation to Enhance Spinal Fusion, Neurosurg. Focus, 2002, 13(6):1-7.

Norris, Management of Postpartum Hemorrhage, American Family Physician, 1997, 55(2):635-640.

Ogurtsov, et al., Development of a Specialized Pacemaker for Use in Obstetrics and Gynecology, All-Union Institute of Medical Instrumentation, Moscow, Translated From Meditsinskaya Technika, 1986, 6:27-31.

Reyal, et al., Severe Post-Partum Hemorrhage: Descriptive Study at the Robert-Debre Hospital Maternity Ward, J. Gynecol. Obstet. Biol. Reprod., 2002, 31:358-364 [English Abstract Included].

Reynolds, The Effect of Certain Calcium Salts on the Rhythmically Contracting and Quiescent Uterine Fistula, With Observations on the Action of Posterior Pituitary Extracts, Am. J. Physiol.—Legacy Content, 1933, 105(2):358-365.

Rizvi, et al., Successful Reduction of Massive Postpartum Haemorrhage by Use of Guidelines and Staff Education, BJOG: An International Journal of Obstetrics and Gynaecology, 2004, 111:495-498.

Sanderson, The Electrical Response to Stimulation of Muscle, and its Relation to the Mechanical Response, J. Physiol., 1895, 18(1-2):117-160.7.

Shafik, et al., Vesical Pacing: Pacing Parameters Required for Normalization of Vesical Electric Activity in Patients With Overactive Bladder, Frontiers in Bioscience, 2004, 9:995-999.

Sultatos, Mechanisms of Drugs That Affect Uterine Motility, Journal of Nurse-Midwifery, 1997, 42(4):367-370.

Svanstrom, et al., Signs of Myocardial Ischaemia After Injection of Oxytocin: A Randomized Double-Blind Comparison of Oxytocin

(56) References Cited

OTHER PUBLICATIONS and Methylergometrine During Caesarean Section, British Journal of Anaesthesia, 2008, 100 (5):683-689.

Thomas, et al., Haemodynamic Effects of Oxytocin Given as i.v. Bolus or Infusion on Women Undergoing Caesarean Section, British Journal of Anaesthesia, 2007, 98(1):116-119.

Webster, Design of Cardiac Pacemakers, Copyright 1995 by the Institute of Electrical and Electronics Engineers, Inc. [Title Page and Table of Contents Only].

Weingarten, et al., Postpartum Uterine Atony After Intravenous Dantrolene, Anesth. Analg., 1987, 66:269-270.

World Health Organization, The Prevention and Management of Postpartum Haemorrhage, Report of a Technical Working Group, Geneva, Jul. 3-6, 1989, 39 pages.

PCT International Search Report and Written Opinion, PCT/US2010/044907, dated Sep. 22, 2010.

PCT International Search Report and Written Opinion, PCT/US2010/030302, dated Nov. 10, 2010.

PCT International Search Report and Written Opinion, PCT/US2011/057856, dated Apr. 16, 2012.

PCT International Search Report and Written Opinion, PCT/US2013/041855, dated Aug. 12, 2013.

\* cited by examiner

O – CURRENT TURNED ON
X – CURRENT TURNED OFF

NOTE: LENGTH L = 6.500 millimeters

UTERINE ELECTRICAL STIMULATION SYSTEM AND METHOD

RELATED APPLICATIONS

This application is a divisional of U.S. patent application 14/609,093, filed Jan. 29, 2015, which is a divisional of U.S. patent application 13/881,812, filed Apr. 26, 2013, which represents the national stage entry of PCT International Application No. PCT/US2011/057856 filed on Oct. 26, 2011, and claims priority under 35 U.S.C. § 119 to U.S. Provisional Patent Application No. 61/407,397 filed on Oct. 27, 2010, all of which are incorporated herein by reference.

STATEMENT REGARDING FEDERALLY SPONSORED RESEARCH

N/A.

BACKGROUND OF THE INVENTION

The present application is directed to systems and methods for applying stimulating current to a patient for treating insufficient uterine contractions.

Postpartum hemorrhage, which is a significant source of maternal morbidity and mortality in modern obstetrics, occurs in up to 18 percent of births (1,2). Even with appropriate management, approximately 3-4 percent of vaginal deliveries result in severe postpartum hemorrhage in the United States and in other developed nations (3), which can result in occult myocardial ischemia, dilutional coagulopathy, and death (4). While sudden death can occur from rapid and uncontrolled postpartum hemorrhage because of brisk blood loss, many deaths are the result of ineffective management of continuous low-level bleeding (5). In less-developed countries and in rural areas of the United States, maternal hemorrhage is a greater issue. For example, in Zimbabwe, hemorrhage is responsible for 25 percent of maternal deaths. Approximately 125,000 women per year die worldwide due to postpartum hemorrhage (6).

Uterine atony causes more than 90 percent of cases of postpartum hemorrhage (5). Uterine atony is a loss of tone in the uterine musculature postpartum, resulting in the failure of uterine muscles to contract tonically and stop postpartum bleeding. This may be related to the inability of myometrial cells in some patients to act properly as pacemakers for tonic (or phasic) contractions after delivery (7), or may be related to changes in threshold or resting potentials brought on by the delivery process or by administration of medications (8).

Normally, contraction of the uterine muscle compresses the vessels and reduces blood flow after delivery. This increases coagulation, which prevents bleeding. However, lack of uterine muscle contractions can cause an acute postpartum hemorrhage. Many factors can contribute to the loss of uterine muscle tone, including overdistention of the uterus, multiple gestations, polyhydramnios, fetal macrosomia, prolonged labor, oxytocin augmentation of labor, grand multiparity (having given birth 5 or more times), precipitous labor (labor lasting less than 3 hours), magnesium sulfate treatment of preeclampsia, chorioamnionitis, halogenated anesthetics, and uterine leiomyomata (9).

Current treatments for preventing blood loss during uterine atony and/or uterine rupture include radical procedures such as surgery, manual massage, which is often minimally effective, and drugs, such as oxytocin, prostaglandins, and ergot alkyloids. Oxytocin and other drug treatment is a common global application, however such treatment is often not well controlled and can have dangerous side effects for both the mother and the fetus.

SUMMARY OF THE INVENTION

The present invention provides a system for treating insufficient uterine contractions in a patient after labor and delivery. The system includes one or more stimulation electrodes coupled to or positioned along one of a uterus, a cervix, a vaginal wall, and an abdominal wall of a patient to apply stimulating current to the patient in order to treat insufficient uterine contractions, and more specifically, for the patient to produce tonic uterine contractions. The stimulation electrodes can be part of a balloon electrode array device, a ring electrode array device, an electrode probe device, and/or a mesh electrode array device. The system can also include electronics for generating and providing the stimulating current to the stimulation electrodes. Some aspects of the invention also provide a connector and cable device for coupling the stimulation electrodes to the electronics.

In one aspect of the invention, a balloon electrode array device includes at least one balloon, an access tube extending into the at least one balloon, a plurality of lead wires routed through the access tube and into an inside portion of the balloon, and a plurality of electrodes. Each one of the plurality of electrodes is coupled to one of the plurality of lead wires, and the plurality of electrodes extend from the inside portion of the balloon to an outer surface of the balloon.

In another aspect of the invention, a mesh electrode array device includes a non-conductive mesh material with a plurality of segments and nodes of intersection of the plurality of segments. The mesh electrode array device also includes a plurality of electrodes, where each one of the plurality of electrodes is coupled to one of the nodes of intersection, and a plurality of lead wires. Each one of the plurality of lead wires is coupled to one of the plurality of electrodes.

Other aspects of the invention include an electrode probe device and a ring electrode array device. The electrode probe device includes a substantially cylindrical probe with a first end and an opposite second end, at least one electrode positioned adjacent to the first end, and at least one lead wire electrically coupled to the at least one electrode. The ring electrode array device includes a flexible ring, a plurality of electrodes affixed to an outer surface of the flexible ring, and a plurality of lead wires electrically coupled to the electrodes.

In yet another aspect of the invention, a connector device includes an electronics connector plug capable of being releasably coupled to a system that produces stimulating current and configured to receive the stimulating current from the system. The connector device also includes a lead wire connector plug capable of being releasably coupled to an electrode device and configured to deliver the stimulating current to the electrode device, and a flexible, electrically insulated cable electrically connecting the electronics connector plug and the lead wire connector plug.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
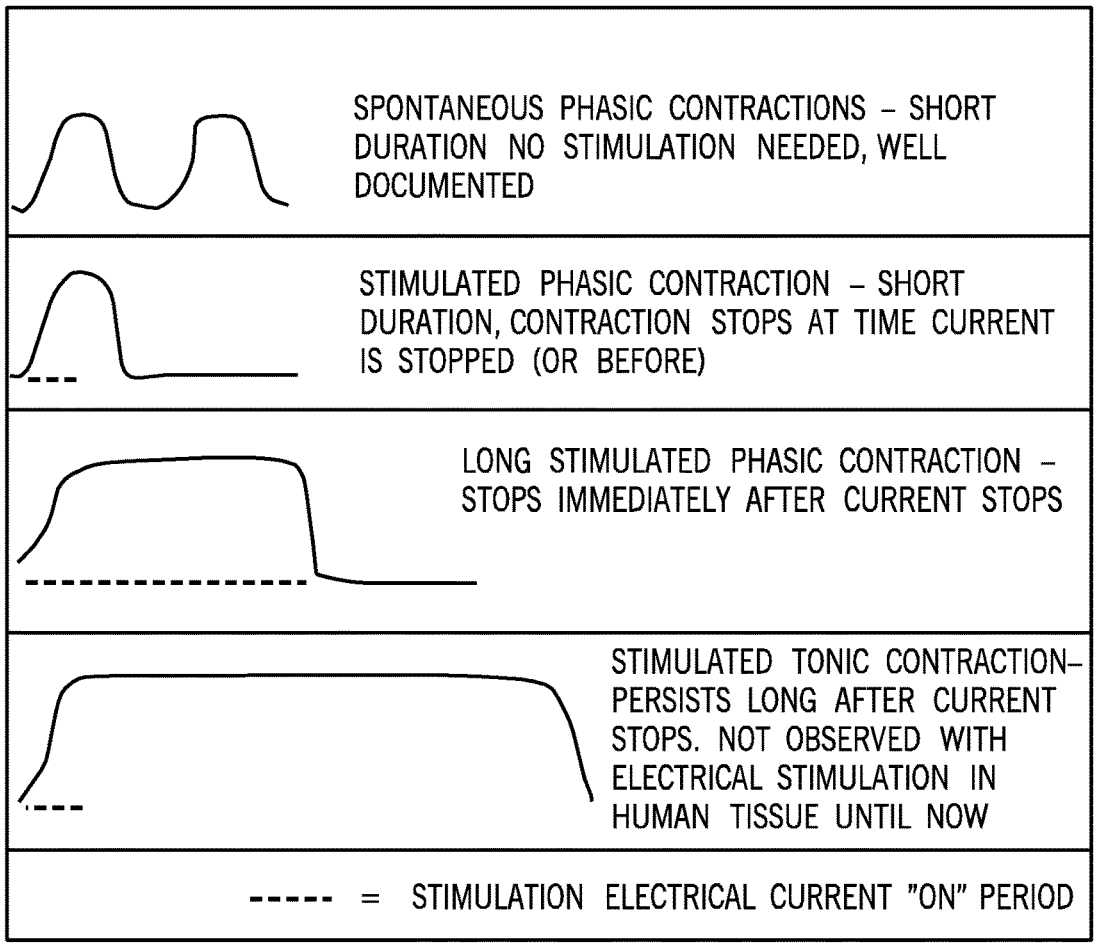
FIG. 1 illustrates different types of observable uterine contractile events.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings. Where appropriate, the terms "stimulation" and "stimulated" are understood to refer to electrical stimulation and electrically stimulated, respectively.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

Some embodiments of the invention provide a system and method of treating uterine atony by administering electrical stimulation to the uterus. The electrical stimulation to the uterus can result in uterine muscle contractile activity, which can aid in decreasing and/or stopping uterine bleeding.

Figure 2:
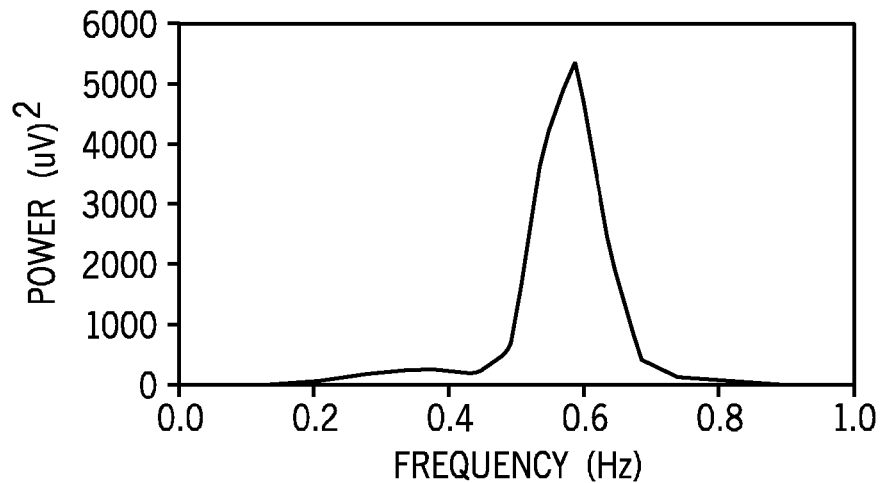
FIG. 2 is a graph illustrating a measured electrical power of contracting uterine muscles at different action potential frequencies.

There are several different types of observable uterine contractile events. As shown in FIG. 1, some uterine contractile events can include spontaneous phasic contractions (spontaneous contractions which are short in duration and occur without outside stimulation), short stimulated phasic contractions (stimulated contractions which are shorter in duration and stop at or before the time stimulation is stopped), long stimulated phasic contractions (stimulated contractions which are longer in duration and stop immediately after the time stimulation is stopped), and tonic contractions (sustained contractions which persist long after stimulation is stopped). During labor and delivery, the human uterus exhibits spontaneous phasic contractions that produce associated electrical action potential frequencies in the range of 0.0 Hertz (Hz) to about 3.0 Hz. In addition, to a lesser degree, the human uterus also exhibits spontaneous phasic contractions during menstrual cycles in non-pregnant women. As shown in FIG. 2, electrical power output of human uterine spontaneous phasic contractions is mostly concentrated at less than 1.0 Hz. Very little electrical power is observed in higher frequencies than the above described range.

Current stimulation systems are used for stimulating the uterine tissue with similar frequencies as those seen naturally, using an external power source to induce contractions in laboring women who experience insufficient contractions to adequately deliver a baby. For example, U.S. Pat. No. 6,356,777, the entire contents of which is incorporated herein by reference, specifies the use of electrical stimulating frequencies in the 0.0 Hz to about 5.0 Hz range for controlling phasic contractions. The uterus responds favorably to such electrical stimulation signals by exhibiting stimulated phasic contractions, like those occurring naturally during labor and delivery, as shown in FIG. 3.

Figure 3:
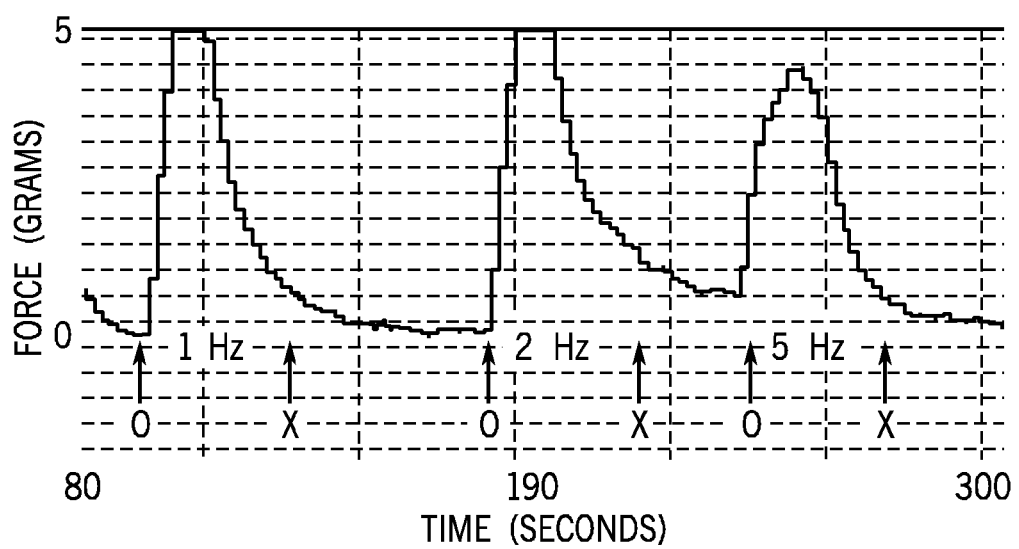
FIG. 3 is a graph illustrating forces exerted by contracting uterine muscles over time when stimulating current is applied at different pulse frequencies.

FIG. 3 illustrates uterine muscle activity over time when a stimulation current is applied. As shown in FIG. 3, uterine muscle action returns to baseline immediately after the current is switched off when using frequencies up to about 5 Hz. In some instances, the maximal contractile activity begins to fall well before the current is turned off, which is indicative of stimulated phasic contractile activity. The stimulated phasic contractile activity shown in FIG. 3 can be considered short stimulated phasic contractions, as the stimulation duration is substantially small (e.g., less than about 3 minutes) and the stimulation frequency lies within the conventional uterine stimulation frequency range. In some embodiments, short stimulated phasic contractions can be specified as having a minimal duration time of about 30 seconds and a maximum duration time of about 3 minutes. Uterine muscle stimulation within these established ranges and the resulting phasic contractile activity are not thought to be useful for stopping uterine blood loss in the case of uterine rupture and postpartum hemorrhage.

Figure 4:
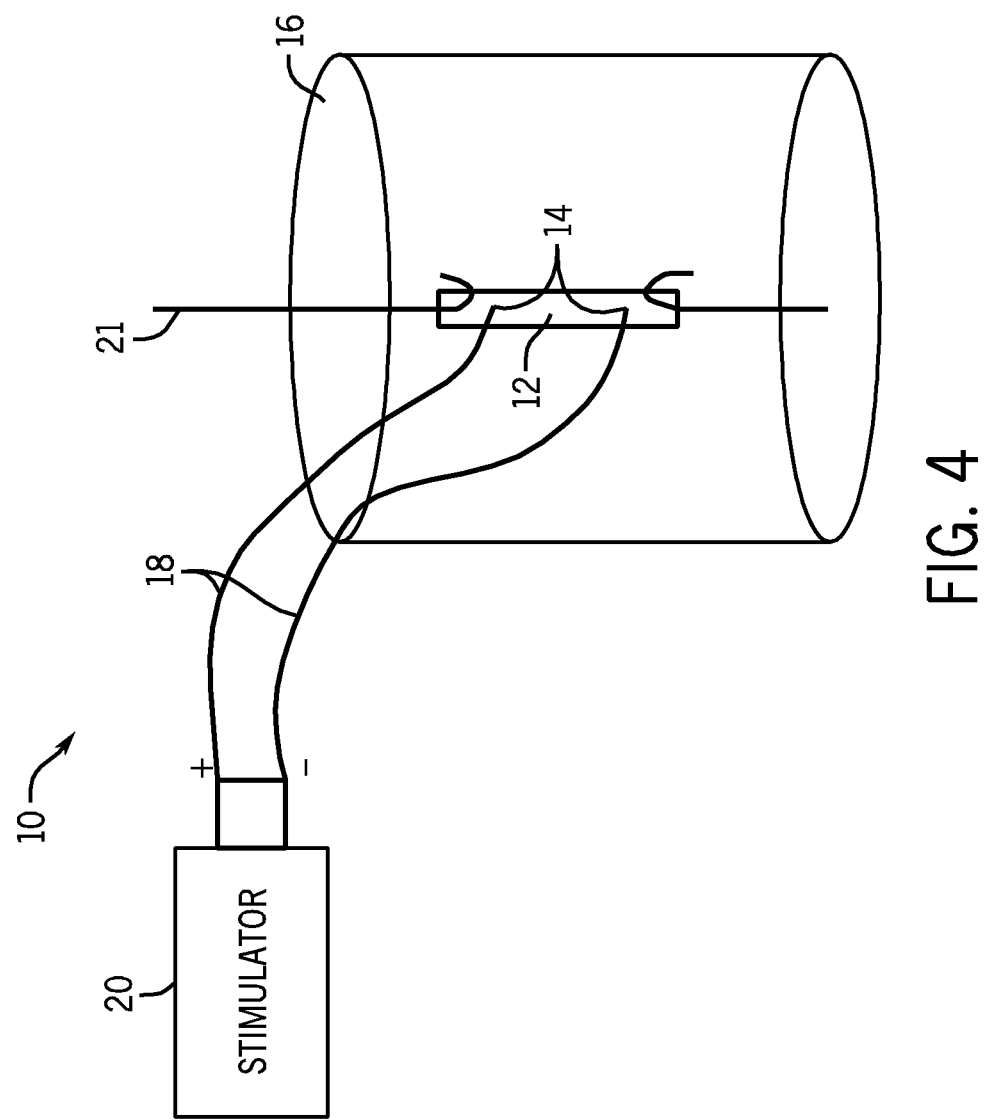
FIG. 4 is a schematic of an in vitro setup for stimulating uterine tissue and measuring resulting contractile activity.

FIG. 4 illustrates an in vitro setup 10 for stimulating uterine tissue and measuring resulting contractile activity. The setup includes one or more strips 12 (i.e., strips of uterine muscle tissue) outfitted with a plurality of stimulation electrodes 14 at each end (i.e., through suturing) isolated in a bath 16 of Krebs solution. Electrode lead wires 18 are Teflon-coated so as to act as insulation from the Krebs solution to prevent shorting of electrical current. The setup 10 also includes a source 20 for providing electrical stimulation with varying parameters. Tension force of the strips are recorded using a transducer (e.g., force gauge 21) and a computer obtains force data sensed by the transducer for analysis and display. The following paragraphs describe force data obtained from setups similar to that described with reference to FIG. 4, using tissue of pregnant patients in labor or after delivery.

Figure 5:
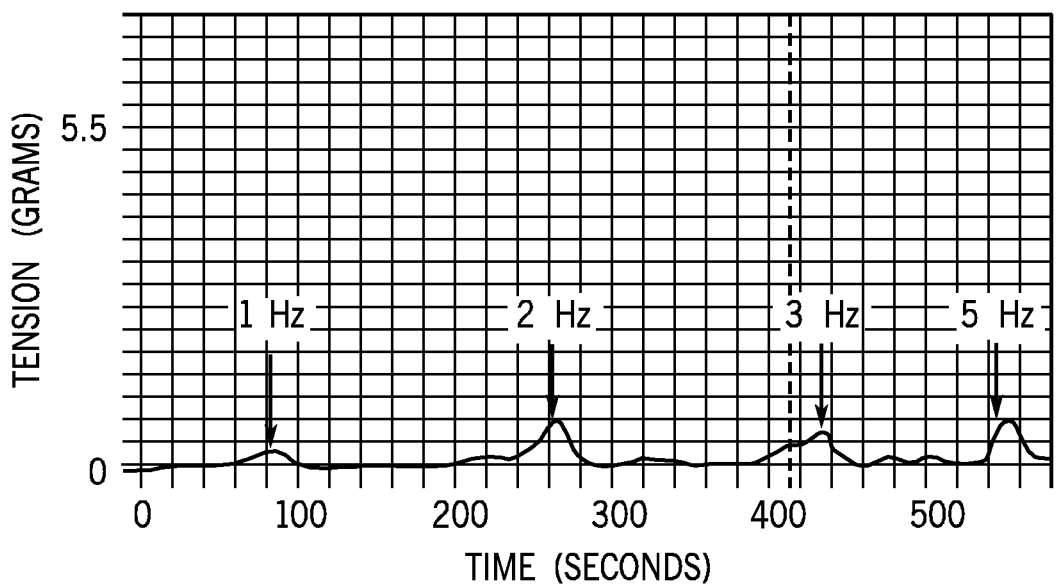
FIG. 5 is a graph illustrating a contractile recording of rat uterine tissue when varying pulse frequency in applied stimulation current.
Figure 6:
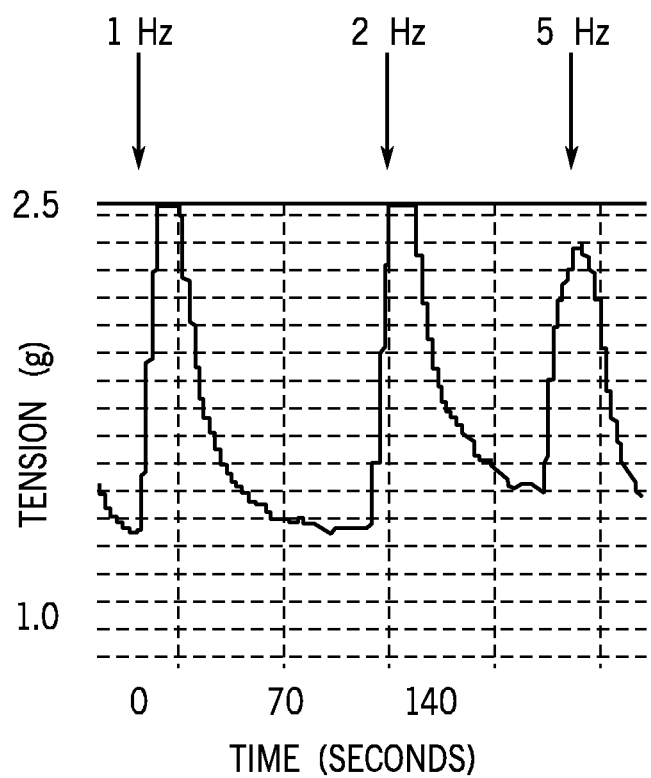
FIG. 6 is a graph illustrating a contractile recording of human uterine tissue, when varying pulse frequency in applied stimulation current.
Figure 7:
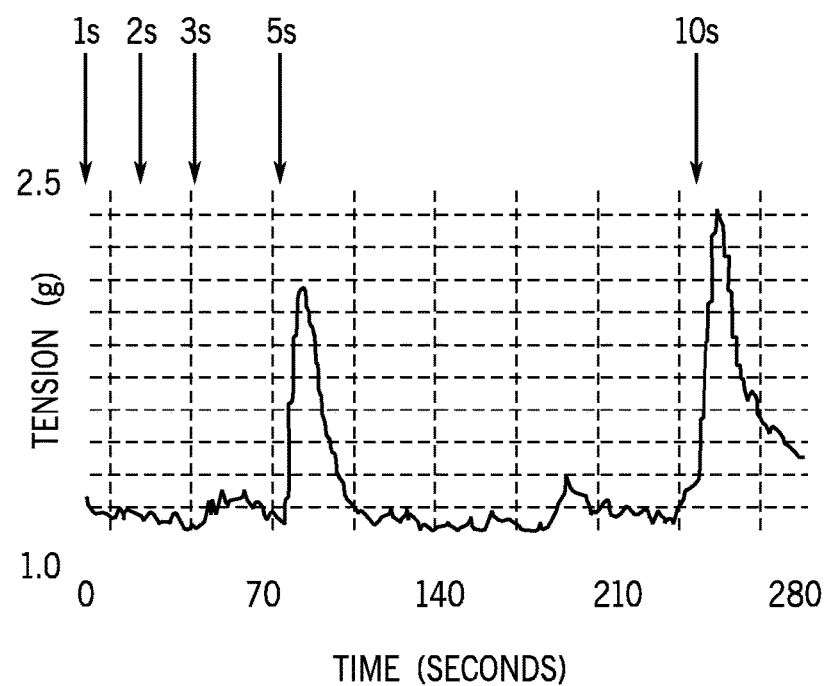
FIG. 7 is a graph illustrating a contractile recording of human uterine tissue, when varying train duration in applied stimulation current.

FIG. 5 illustrates resulting force data from a test strip 12 of rat uterine tissue, when varying the stimulation current frequency (at 1 Hz, 2 Hz, 3 Hz, and 5 Hz), with stimulation voltage and train duration fixed. Each frequency tested produced a visible contractile response, resulting in short stimulated phasic contractions. FIG. 6 illustrates resulting force data from a test strip 12 of human uterine tissue, with stimulation current frequency varied (at 1 Hz, 2 Hz, and 5 Hz), with stimulation voltage and train duration fixed. Each frequency tested produced a short stimulated phasic contraction. FIG. 7 illustrates resulting force data from a test strip 12 of human uterine tissue, with stimulation current train duration varied (at 1 second, 2 seconds, 3 seconds, 5 seconds, and 10 seconds), with stimulation voltage and frequency fixed. No noticeable response was seen from 1-second and 2-second train durations. However, train durations of 3 seconds, 5 seconds, and 10 seconds produced short stimulated phasic contractions. The short stimulated phasic contractions shown in FIGS. 5-7, while useful for inducing or augmenting labor in women whose uterine function is insufficient for successful labor and delivery, are not useful for stopping blood loss during uterine atony and postpartum hemorrhage.

Figure 8:
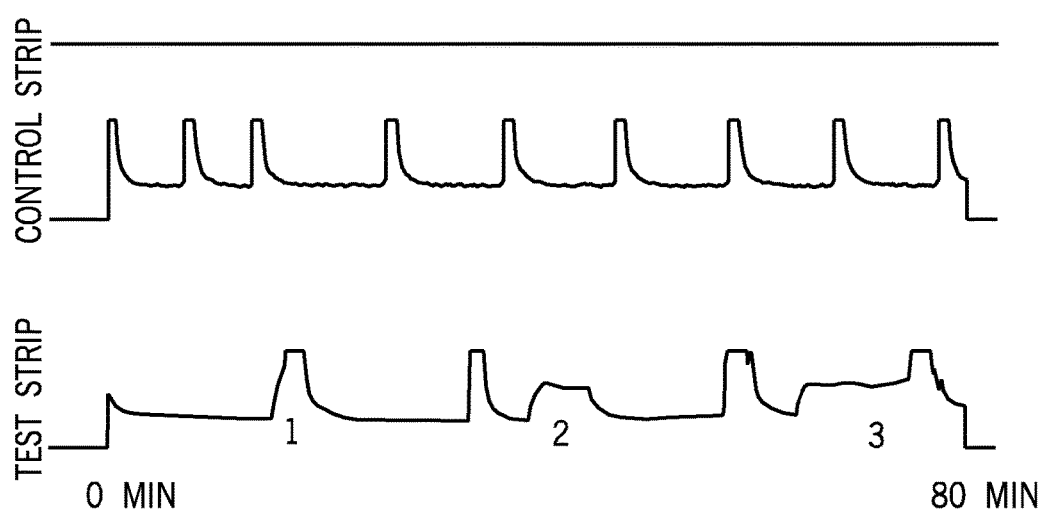
FIG. 8 is another graph illustrating contractile recordings of human uterine tissue, including a control trace and a test trace, when varying train duration in applied stimulation current.

FIG. 8 illustrates resulting force data from test and control strips 12 of human myometrial tissue that were obtained from a term patient (39 weeks gestation) who demonstrated insufficient contractile activity during labor. Electrical stimulation at about 10 volts in pulses of about 2 Hz were applied to the test strip 12. The pulses were run for a 5 minute duration (period 1), a 10 minute duration (period 2), and a 20 minute duration (period 3). FIG. 8 shows spontaneous phasic contractile activity in the control strip 12 (top trace, no outside electrical stimulation provided), and spontaneous phasic contractile activity as well as stimulated phasic contractile activity in the test strip 12 (bottom trace, outside electrical stimulation provided by the source 20). The test strip 12 produced stimulated phasic contractile activity during period 1, period 2, and period 3 as a result of direct electrical stimulation of the test tissue. The duration of the stimulated phasic contractile activity was in direct proportion to the duration of the electrical stimulation current applied, and when the electrical stimulation current was turned off, the test strip force measurement returned fully to baseline, illustrating complete relaxation of the tissue.

The stimulated phasic contractile activity shown in FIG. 8 can be considered long stimulated phasic contractions, as the stimulation duration is longer than about 3 minutes and the stimulation frequency lies within the conventional uterine stimulation frequency range. In some embodiments, long stimulated phasic contractions may be effective for reducing bleeding during postpartum hemorrhage and uterine atony, however, the amount of electrical energy required, and the length of time that the uterine tissue is exposed to such energy, may be too large to be of practical value in other embodiments.

Figure 9:
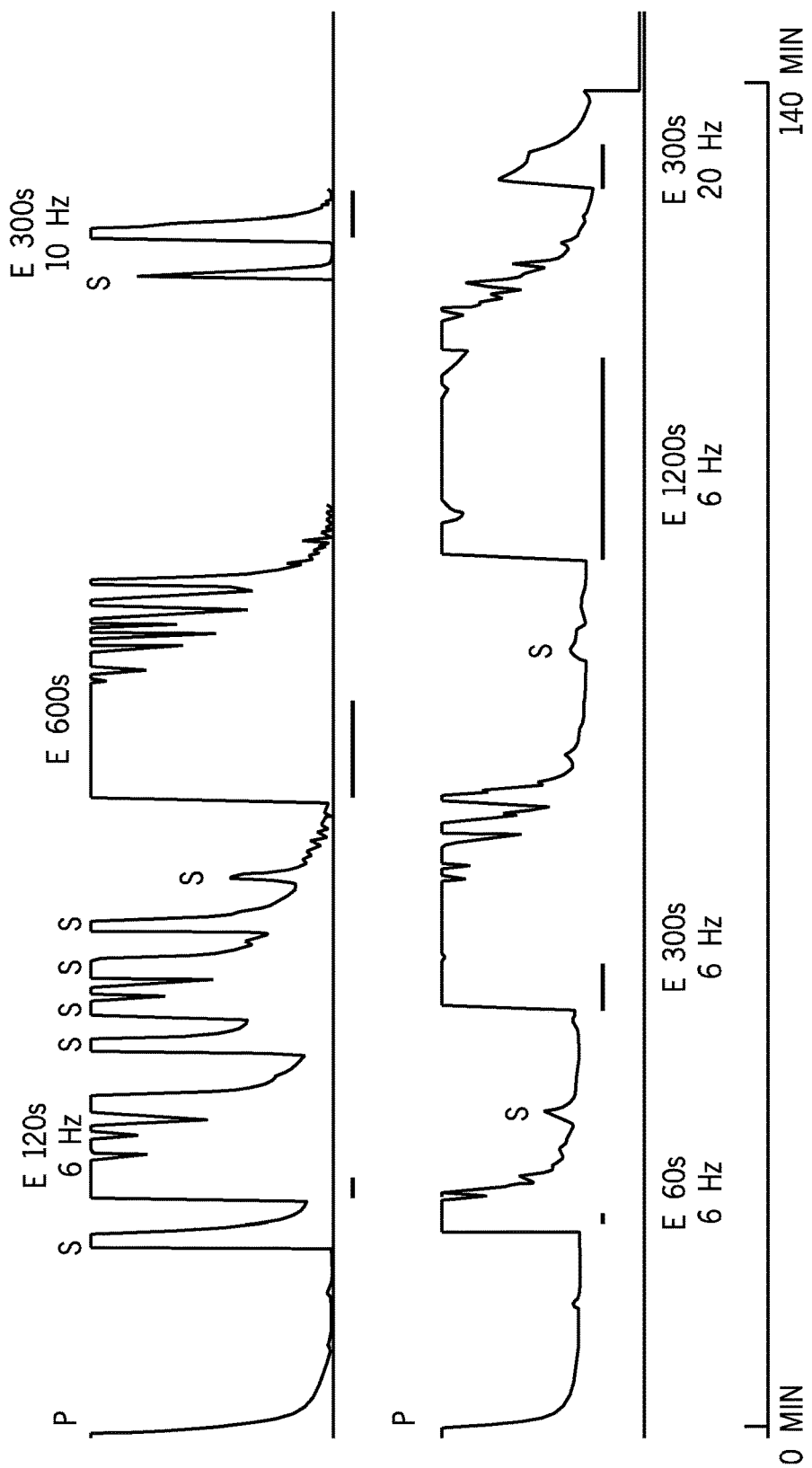
FIG. 9 is another graph illustrating contractile recordings of human uterine tissue, when varying pulse frequency outside conventional parameters in applied stimulation current, in accordance with the present invention.

FIG. 9 illustrates resulting force data from two test strips 12 of human uterine tissue, with electrical stimulation frequencies varied (at 6 Hz, 10 Hz, 20 Hz) and with electrical stimulation current pulse train duration varied (at 60 seconds, 120 seconds, 300 seconds, 1200 seconds). Spikes shown in FIG. 9 indicate uterine muscle contractions. The spikes labeled "P" indicate initial preparatory contractions. The spikes labeled "S" indicate spontaneous uterine phasic contractions. The solid bars under the long spikes indicate the time periods during which electrical stimulation currents were applied to the uterine muscles. These time durations of electrical stimulation are indicated above the long spikes (in seconds) following the letter "E". While frequencies greater than or equal to about 5.0 Hz lie outside of the established range of frequencies normally associated with uterine electrical activity, they are capable of producing a muscle response in the form of sustained uterine contractions. These contractions can be considered tonic contractions (a type not observed during labor and delivery or using electrical stimulation on the uterus within established frequencies). As shown in FIG. 9, these tonic contractions remain forceful well after the treatment has stopped (i.e., after the applied electrical current has been turned off). In some embodiments, these tonic contractions (i.e., forceful and sustained contractions) or tetanic contractions (i.e., tonic contractions which remain maximally, or near-maximally, forceful) can be very useful for stopping blood loss during uterine atony and uterine rupture.

Tonic contractile events are not possible to achieve using conventional electrical stimulation parameters (i.e., 0.0 Hz to about 5.0 Hz), which only seem capable of producing phasic contractions of the type observed during labor and delivery. Also, presently available drugs and systems, including oxytocin, are not capable of producing sustained, forceful contractions after treatment with them has completed. In some embodiments, only tonic contractions, achieved using frequencies at or above about 5.0 Hz, can be useful for contracting the uterus during critical bleeding in women with uterine atony and/or uterine rupture. These types of contractions can help reduce the bleeding to allow doctors enough time to stabilize the patient with other methods (e.g., to suture the uterus if needed without having to perform more radical surgery, like a hysterectomy), or can help stop the bleeding completely on their own.

Figure 10:
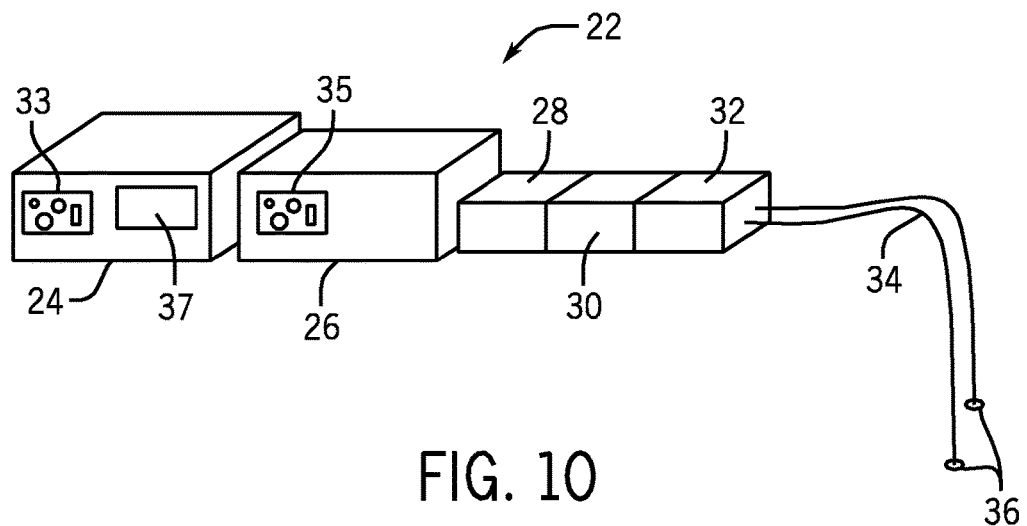
FIG. 10 is a schematic view of a system for use with the present invention.

FIG. 10 illustrates a system 22 according to one embodiment of the invention. The system 22 can stimulate uterine muscles into tonic contractions using frequencies greater than about 5.0 Hz. The system 22 can be used to stimulate muscles of the uterus in a way that does not affect other organs and can be accurately regulated and controlled, unlike oxytocin or other conventionally-used drugs. The system 22 can be used on a patient, such as a female post-partum, and can be controlled by a user, such as a physician or medical staff member. For example, the system 22 can input innocuous electrical pulses into the patient's uterus with sufficient effect to incite postpartum tonic or tetanic contractions in order to help treat uterine atony and postpartum hemorrhage. In some embodiments, the system 22 can include a control module 24, a current source 26, an isolation unit 28, a constant maximum current unit 30, a biphasic converter 32, a set of lead wires 34, and a set of electrodes 36.

The control module 24 can contain computing capability, software, and memory. The control module 24 can be set using interface controls 33, such as dials, switches and/or auxiliary inputs, to perform preprogrammed stimulation tasks, including commanding the current source 26 to output stimulation current of selected frequency, amplitude, pulse width, and train duration automatically for selected periods of time. The control module 24 can also be operated manually by the user, in which the user can determine and set one or more output stimulation currents of desired frequencies, amplitudes, pulse widths, and train durations as needed spontaneously (i.e., in real time or in near-real time). For example, the control module 24 can be operated automatically or manually to produce a stimulation current which can cause tonic or tetanic contractions of the patient's uterine muscle, and the user has the capability to adjust the stimulation current parameters (i.e., frequencies, amplitudes, pulse widths, and/or train durations) in real time or near-real time during observation of the patient's uterus.

In one embodiment, the control module 24 can automatically or manually operate multiple stimulation outputs of the current source 26 independently or in unison with varying or similar current frequencies, amplitudes, pulse widths, and train durations. As a result, the control module 24 can provide stimulation currents directly to the uterus or through various organs, such as the cervix, vaginal wall and/or abdominal wall separately, simultaneously, or sequentially, or can provide stimulation currents to various parts of the uterus separately, simultaneously, or sequentially.

In one embodiment, pre-recorded uterine electrical traces, obtained from normally contracting patients and saved digitally, can be stored in the control module 24 to be used, in turn as the electrical current trace patterns for commanding the current source 26 to output identical stimulation current to patients with abnormal uterine activity, such as patients with insufficient or absent contractile activity during postpartum hemorrhage. In addition, artificially generated current traces, saved digitally, with known frequencies, amplitudes, pulse widths, and train durations, can be stored in the control module 24 to be used as the electrical current trace patterns for commanding the current source 26 to output identical stimulation current to patients with abnormal uterine activity during postpartum hemorrhage.

In another embodiment, the control module 24 can automatically regulate and modify the electrical current output produced by the current source 26 based on input from electrical contractile activity of the patient's uterus, which can be transmitted to the control module 24 via pick-up wires, a signal conditioner, and/or after-conditioning wires (not shown). The control module 24 can regulate and modify the produced electrical current by changing the electrical stimulation pulse-width, current amplitude, pulse train duration, and/or the pulse frequency according to a pre-programmed algorithm.

In some embodiments, the control module 24 can include a display 37 (as shown in FIG. 10), such as a video display, a digital display, light-emitting diode (LED) display, etc., to display the stimulation output currents produced for the user to read or assess. The control module 24 can be coupled to the current source 26 by wires, direct electrical coupling, or another suitable coupling. For example, in one embodiment, the control module 24 can communicate with the current source 26 via a wireless connection, such as Bluetooth®.

The current source 26 can generate the output stimulation current. In one embodiment, the electrical stimulation current settings can be adjusted manually at the current source 26 by the user using interface controls 35, such as dials, switches or other devices. In another embodiment, the electrical stimulation settings can be controlled by the control module 24 (e.g., as preprogrammed settings or by the user using the interface controls 33, as described above), and output to the current source 26. As described above, in some embodiments, the current source 26 can output multiple electrical stimulation currents either directly to the uterus or indirectly to the uterus via the cervix, the vaginal wall and/or the abdominal wall separately, simultaneously, or sequentially, as commanded by the control module 24, or the current source 26 can output multiple electrical stimulation currents to various locations of the uterus separately, simultaneously, or sequentially.

In some embodiments, there can be a constant two-way communication between the current source 26 and the control module 24, so that the current source 26 can receive commands from the control module 24 and the control module 24 can receive actual output current values from the current source 26.

In some embodiments, the current source 26 can be capable of generating an output current between about 0.01 milliamperes and about 100.00 milliamperes (with possible voltages between about 0.0001 volts and about 100 volts). Pulse widths of the current can be adjusted between about 0.1 millisecond and about 1000 milliseconds. Frequencies of the current can be adjusted from about 0.1 Hertz to about 30 Hz or greater, or about 100 Hz or greater. Pulse train durations can be adjusted from about 1 second to about 10,000 seconds. In addition, output currents can be sinusoidal so as to reduce tissue damage and maximize effect (10). In one embodiment, the current source 26 can produce a maximal "jolt" of uterine electrical stimulation energy equivalent to between about 1 Joule and about 120 Joules of electrical energy in a short duration between about 1 millisecond and about 1000 milliseconds. Further, the electrical stimulation current output from the current source 26 can be sensed, measured, or detected by either the current source 26 or the control module 24 and can be automatically shut off if current values are determined to be dangerous or outside prescribed, programmed, or set values.

The isolation unit 28 can prevent ground loop currents from affecting the patient. In one embodiment, isolation is accomplished through optical isolation. In other embodiments, induction or other methods of isolation can be used by the isolation unit 28.

The constant maximum current unit 30 can allow the user to regulate the amount of maximum current that the patient's uterus receives. The constant maximum current unit 30 can prevent tissue damage due to extreme current fluctuations as tissue resistance varies (11), and can be set (either in a discrete or continuous fashion) to or between values well below human threshold for human feeling (e.g., about 0.01 milliamperes) and values uncomfortable for humans (e.g., about 100 milliamperes). In one example, the constant maximum stimulation current can be set at a value which maximizes current input without damaging tissue and with minimal discomfort to the patient (e.g., about 4 milliamperes).

The biphasic converter 32 can alternate the polarity of current pulses produced by the current source 26 after having moved through the isolation unit 28 and the constant maximum current unit 30 in order to further prevent adverse effects on the patient's tissues. The biphasic converter 32 can insure that the total energy delivered at the tissue site, as integrated over time, has a net value of zero. This can reduce the possibility of heating and subsequent damage to the patient's tissues (11, 12).

The lead wires 34 can transmit the output current from the biphasic converter 32 to the electrodes 36. In one embodiment, the lead wires 34 can be those manufactured by Advantage Medical Cables or similar devices. In some embodiments, the system 22 can include between one and fifty lead wires 34. For example, different lead wires 34 can carry different types or strengths of currents that incite, induce, or augment a tonic contraction at different times in different parts of the uterus, as preprogrammed or set by the user (e.g., to stimulate various parts of the patient's uterus separately, simultaneously, and/or sequentially). In some embodiments, the lead wires 34 can be insulated.

Figure 11:
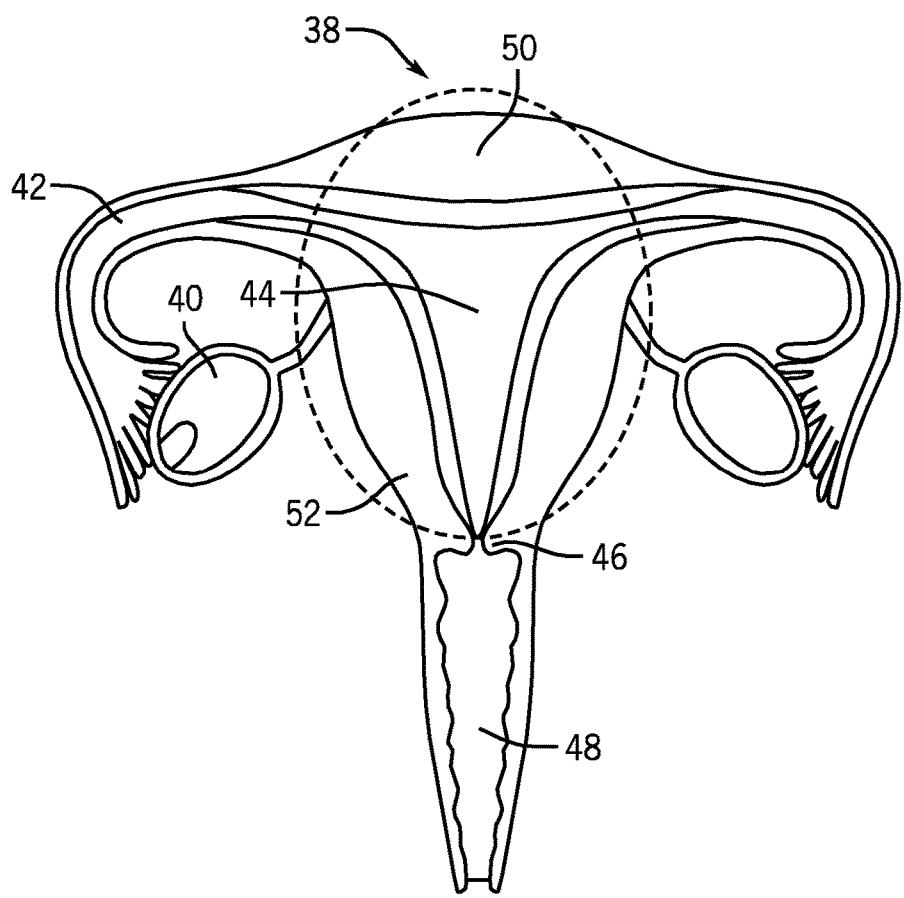
FIG. 11 is a front cross-sectional view of a uterus.

FIG. 11 illustrates a patient's uterus 38, ovaries 40, fallopian tubes 42, a uterine body (or intrauterine cavity) 44, a cervix 46, a vagina 48, a fundus 50 (i.e., top portion) of the uterus, and a distal portion 52 of the uterus. The electrodes 36 can be attached to or near the uterus 38 in a specific orientation and at specific locations that will have the best effect upon uterine contractility for the patient, as determined by the user. In one example, the electrodes 36 can be placed upon the vaginal wall 48 and/or the cervix 46. In another example, the electrodes 36 can be placed at locations across the fundal portion 50 and distal portion 52 of the uterus 38. Also, the electrodes 36 can be mounted externally to the patient's abdominal surface.

The electrodes 36 can be attached to the patient's abdominal surface and/or uterus 38 using biocompatible glue or tissue adhesive, or by suction or other self-affixing electrodes. In one embodiment, the electrodes 36 can be standard silver chloride (AG2Cl) electrodes, EEG electrodes, suction electrodes, or needle electrodes. In some embodiments, the system 22 can include between one and fifty electrodes 36 (e.g., equal to the number of lead wires 34). Different electrodes 36 can be positioned at various locations in or around the patient's uterus 38, where some or each of the electrodes 36 causes tonic and/or phasic effects according to the electrical stimulus applied through them. For example, one or several electrodes 36 can act as a local pacemaker for eliciting contractions, while one or several other electrodes 36 can cover one or many different portions of the uterus 38 for eliciting global tonic or tetanic contractions. In addition, in some embodiments, the electrodes 36 can consist of platinum-iridium metals, so as to reduce the possibility of tissue lesions (12).

Figure 12A:
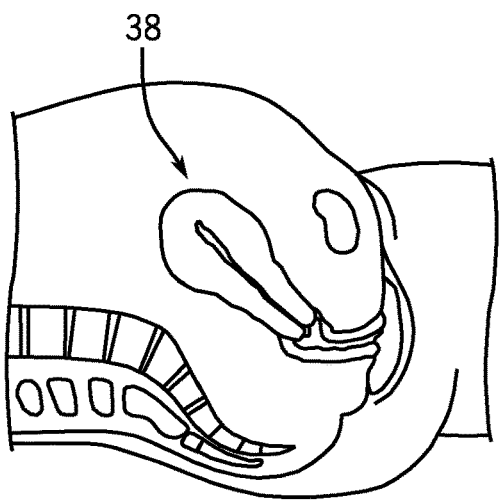
FIG. 12A is a side cross-sectional view of a uterus normally contracting post-partum.
Figure 12B:
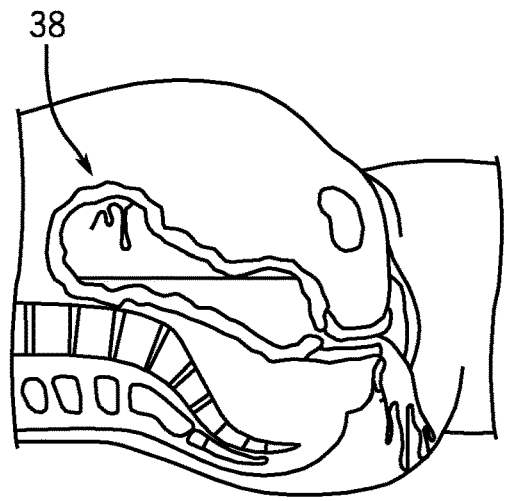
FIG. 12B is a side cross-sectional view of a ruptured uterus, which is not contracting post-partum due to uterine atony.
Figure 12C:
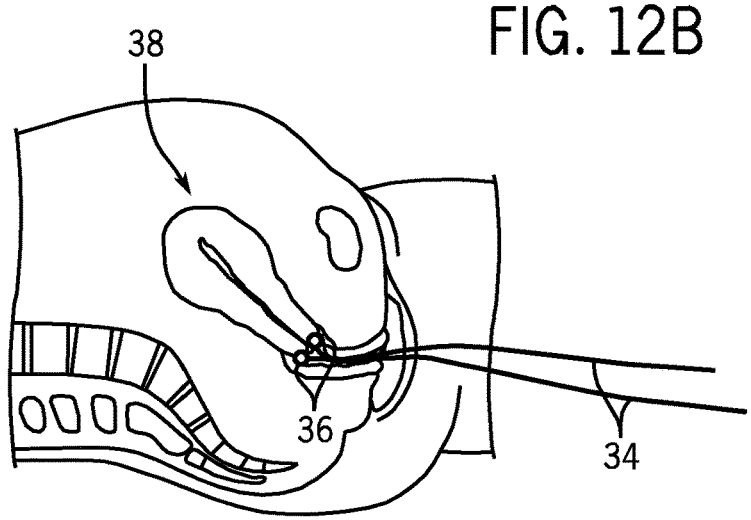
FIG. 12C is a side cross-sectional view of a ruptured uterus being stimulated by the system of FIG. 10.

FIGS. 12A-12C illustrate a patient's uterus 38 in three different conditions. FIG. 12A shows a naturally contracting uterus 38 post-partum. Forceful and spontaneous tonic contractions can prevent blood loss. FIG. 12B shows a uterus 38 which is not contracting postpartum due to uterine atony. The lack of tonic contractile activity allows the uterus to bleed out, threatening the life of the patient. FIG. 12C shows the uterus 38 with atony and uterine rupture treated effectively (i.e., forcefully contracted) using electrical tonic stimulation. As shown in FIG. 12C the uterus 38 has been outfitted with electrodes 36 (trans-vaginally) so that the system 22 can output stimulated current (i.e., through the lead wires 34) for tonic activity using electrical frequencies greater than or equal to about 5 Hz. The artificially-stimulated tonic contractions can help reduce, stop and/or manage the blood loss. In one embodiment, the stimulated current can be output to the patient for a duration greater than about 10 seconds. In some embodiments, the pulse train durations can be up to about 30 minutes long.

In addition, the system 22 can be used in conjunction with other devices, methods, systems, and treatments for postpartum hemorrhage, uterine atony, and bleeding or coagulation problems, including but not limited to oxytocin, prostaglandins, misoprostol, prepidil, ergot alkyloids, tamponades, balloon tamponades, sponges, clamps, manual uterine massage and manipulation, sutures, bio-compatible adhesives, cauterization, and/or pharmaceutical coagulants.

Figure 13:
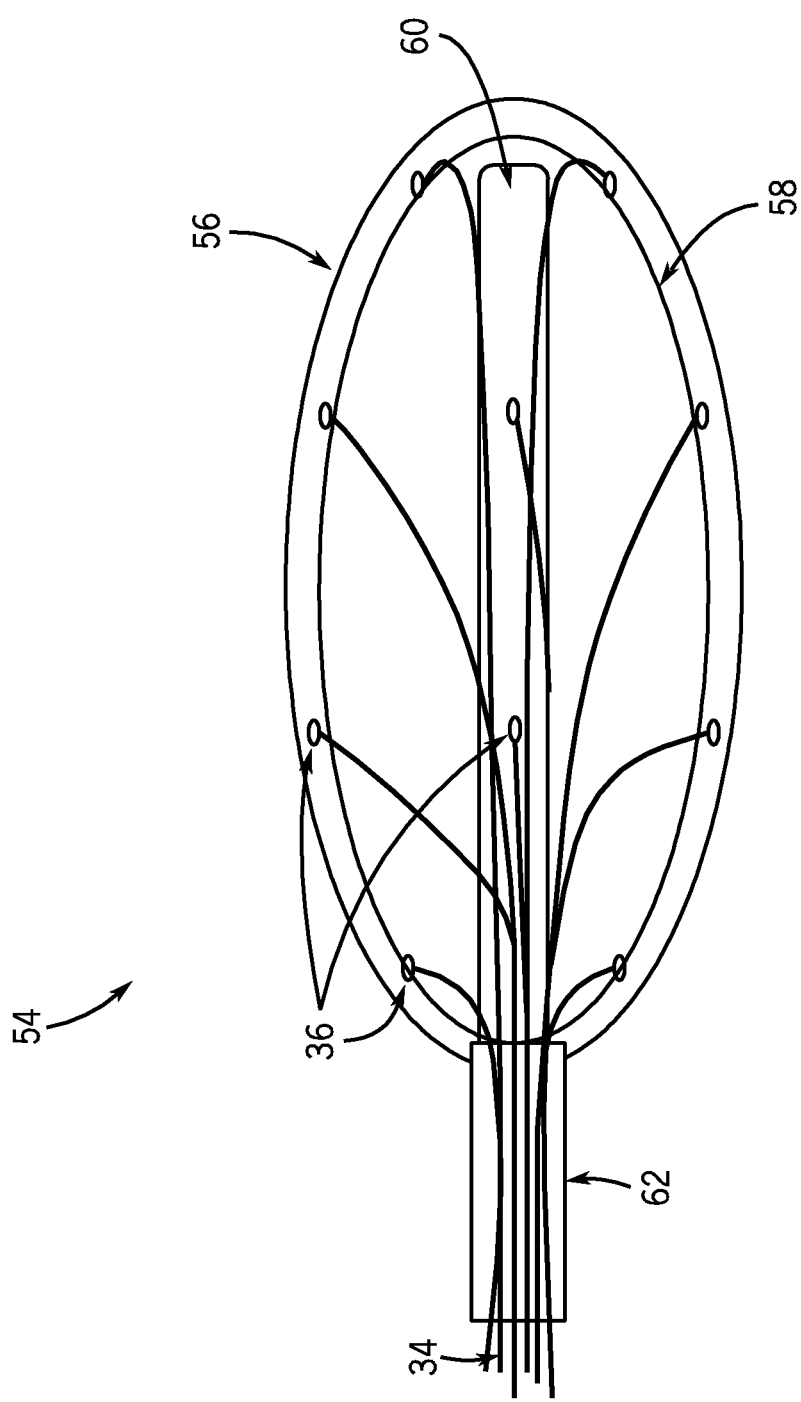
FIG. 13 is a side view of a balloon electrode array device for use with the present invention.
Figure 14B:
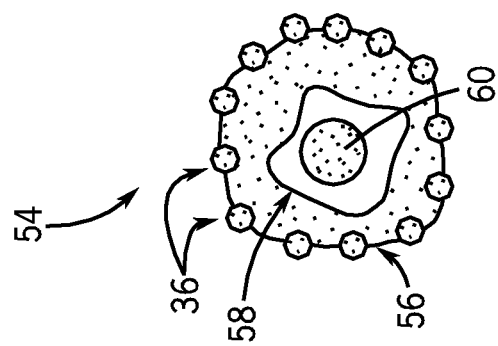
FIG. 14B is a front cross-sectional view of the balloon electrode array device of FIG. 13 in a deflated state.

In some embodiments, the system 22 can include one or more devices for positioning the electrodes 36 within a patient's uterus, as described below. For example, in some embodiments, the system 22 can include a balloon electrode array device 54, as shown in FIGS. 13-14B, outfitted with the lead wires 34 and the electrodes 36. The balloon electrode array device 54 can be used to assist with reducing blood flow from the uterus 38 during postpartum hemorrhage through mechanical pressure as well as electrical stimulation (i.e., using stimulation frequencies greater than or equal to about 5 Hz for inducing tonic or tetanic contractions). Also, in some embodiments, the balloon electrode array device 54 can be used to assist with inducing contractions in laboring women (i.e., using conventional stimulation frequencies for inducing stimulated phasic contractions).

The balloon electrode array device 54 can include a balloon, or concentric balloons, which can be inserted trans-vaginally and trans-cervically. The balloon electrode array device 54 can be inflatable (in order to apply mechanical pressure to the inside wall of the uterus 38) and can alternatively or simultaneously apply electrical stimulation to contract uterine muscle and/or arteries. The inflation of the balloon can provide a reliable contact of the attached stimulating electrodes 36 to the internal surface of the uterus 38. In one embodiment, the balloon electrode array device 54 can be a dual balloon electrode array and internal pressure intrauterine device, as shown in FIG. 13. In one embodiment, the balloon electrode array device 54 can include an outer balloon 56, an inner balloon 58, a set of insulated lead wires 34, a semi-rigid core 60, an inflation/wiring access tube 62, a set of electrodes 36, and a drainage tube (not shown).

In some embodiments, the outer balloon 56 can be made of latex, rubber, silicone, or another biocompatible stretchable polymer or plastic. The outer balloon 56 can be fitted on its outer surface with an arrangement of one or more electrodes 36, which can be distributed evenly about a portion of the outer surface, as shown in FIG. 13. The number of electrodes 36 can be varied in different embodiments. A conductive portion of the electrodes 36 can protrude through the outer surface to an inner surface of the outer balloon 56.

Figure 14A:
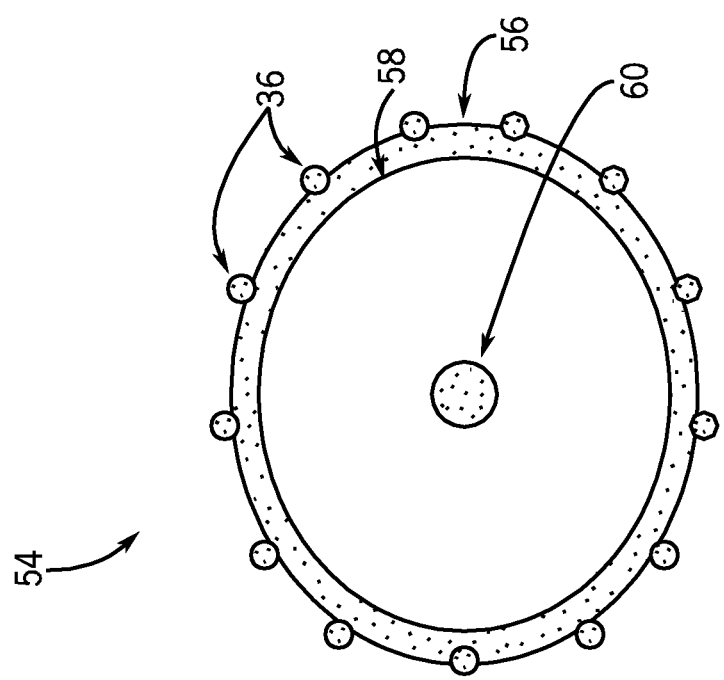
FIG. 14A is a front cross-sectional view of the balloon electrode array device of FIG. 13 in an inflated state.

In some embodiments, the inner balloon 58 can be made of the same material as the outer balloon 56 (e.g., latex, rubber, silicone, or another biocompatible stretchable polymer or plastic). The inner balloon 58 can be airtight and watertight and can be inflated with an inflating material such as a liquid or a gas (e.g., saline, water, or air), as shown in FIG. 14A. Inflation of the inner balloon 58 can cause the outer balloon 56 to also expand. In one embodiment, the balloon electrode array device 54 does not include the inner balloon 58, and the outer balloon 56 can be watertight, airtight, and inflatable (i.e., as a single balloon electrode array and internal pressure intrauterine device).

The set of insulated lead wires 34 can equal the number of electrodes 36, with each individual lead wire 34 carrying electrical stimulation current to an individual electrode 36 fitted in, on, and/or through the outer balloon 56. In one embodiment, each lead wire 34 can be connected to its respective electrode 36 via the conductive portion of the electrode 36 protruding through the outer balloon 58. In addition, the set of lead wires 34 can be positioned in between the inner balloon 58 and the outer balloon 56 (i.e., along the outside of the inner balloon 58 and on the inside of the outer balloon 56), so that the lead wires 34 do not come into contact with the patient's uterus 38.

The semi-rigid core 60 can be rigid enough to facilitate the insertion of the device 54 through the vaginal canal, through the cervix, and into the intrauterine cavity (i.e., in a deflated state, as shown in FIG. 14A), but not so rigid as to cause the balloon electrode array device 54 to perforate the uterine tissue when inserted into the uterus 38. In some embodiments, the semi-rigid core 60 can be hollow, flexible tubing made of rubber, plastic, Tygon®, or other similar materials. Also, in one embodiment, the balloon electrode array device 54 is capable of being placed into the uterus manually by hand without requiring the semi-rigid core 60.

The inflation/wiring access tube 62 can serve as a conduit for introducing the inflating material into the inner balloon 58 (or the outer balloon 56 in some embodiments) and for at least partially routing the set of lead wires 34 from the balloon electrode array device 54 to an external electrical current and voltage source (e.g., indirectly to the current source 26 through the biphasic converter 32 of the system 22, as described above). The drainage tube (not shown) can be used for monitoring and measuring blood flow from the uterus 38. In some embodiments, the balloon electrode array device 54 may not include the drainage tube.

As described above, electrical muscle stimulation can provide a way to specifically apply different contractile effects locally on the uterus 38. The balloon electrode array device 54 (or the other electrode array devices described below) can be used with the system 22 to aid in stimulating uterine contractions at a controllable rate and a controllable strength, as determined by the user, for example, to help produce more contractions or more powerful contractions for efficient and safer deliveries for women in labor or to help incite life-saving uterine contractions in critical hemorrhaging patients after delivery to help treat uterine atony. In the case of hemorrhage and uterine atony, the applied pressure to the cervical area 46, vaginal area 48 and/or intrauterine cavity 44 as a result of inflating the outer balloon 60 can act as an external aid to help control bleeding while the stimulation currents can help incite the patient's natural response to control bleeding (i.e., through tonic contractions of the uterine muscles). Further, in some embodiments, the balloon electrode array device 54 can be used to aid in cervical ripening to help induce labor. The inflated balloon electrode array device 54 can apply pressure to the cervix 46 to help soften the cervix and incite dilation.

In some embodiments, the system 22 can include a ring electrode array device 64, as shown in FIGS. 15A-16B. The ring electrode array device 64 can be a flexible ring outfitted with lead wires 34 and electrodes 36 and inserted transvaginally for assisting with reducing blood flow from the uterus 38 during postpartum hemorrhage through electrical stimulation (i.e., using stimulation frequencies greater than or equal to about 5 Hz for inducing tonic or tetanic contractions). Also, in some embodiments, the ring electrode array device 64 can be used to assist with inducing contractions in laboring women (i.e., using conventional stimulation frequencies for inducing stimulated phasic contractions).

Figure 15A:
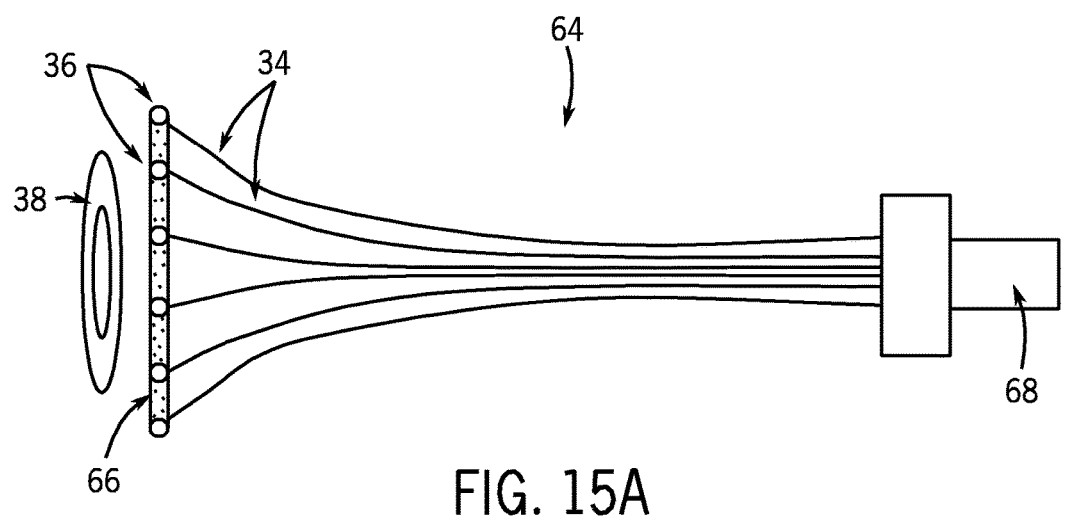
FIG. 15A is a side view of a ring electrode array device for use with the present invention.
Figure 15B:
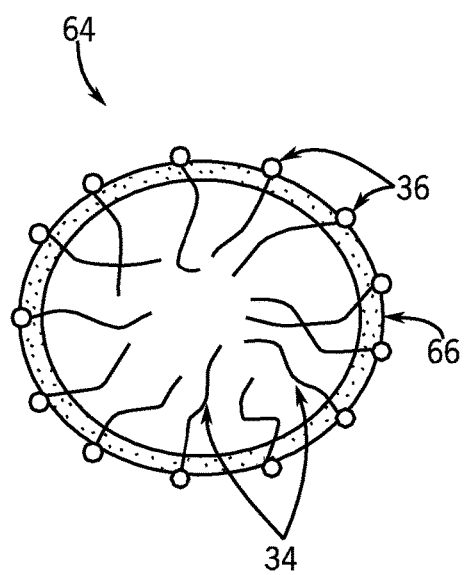
FIG. 15B is a front cross-sectional view of the ring electrode array device of FIG. 15A.

The ring electrode array device 64 can include a ring 66, a set of electrodes 36, and a set of insulated lead wires 34. The ring 66 can comprise ring-shaped or torus-shaped rubber, latex, silicone, Tygon®, or a similar medical grade flexible material which is biocompatible. The set of electrodes 36 can be affixed to the outer surface of the ring 66, or embedded within or incorporated into the ring material so that the electrodes 36 are exposed at an outer surface of the ring 66. The lead wires 34 can be completely external to the ring material or partly affixed to or embedded in the ring material. In some embodiments, the set of lead wires 34 can be separately coupled directly to the system 22 (e.g., to the biphasic converter 32). In other embodiments, the set of lead wires 34 can be separately coupled to a lead cable connector 68, as shown in FIG. 15A, which can be permanently or releasably coupled to the system 22. For example, the ring electrode array device 64 can be disposable so that, after stimulation, the lead wires 34 can be disconnected from the lead cable connector 68 and the entire device 64 disposed of.

Figure 16A:
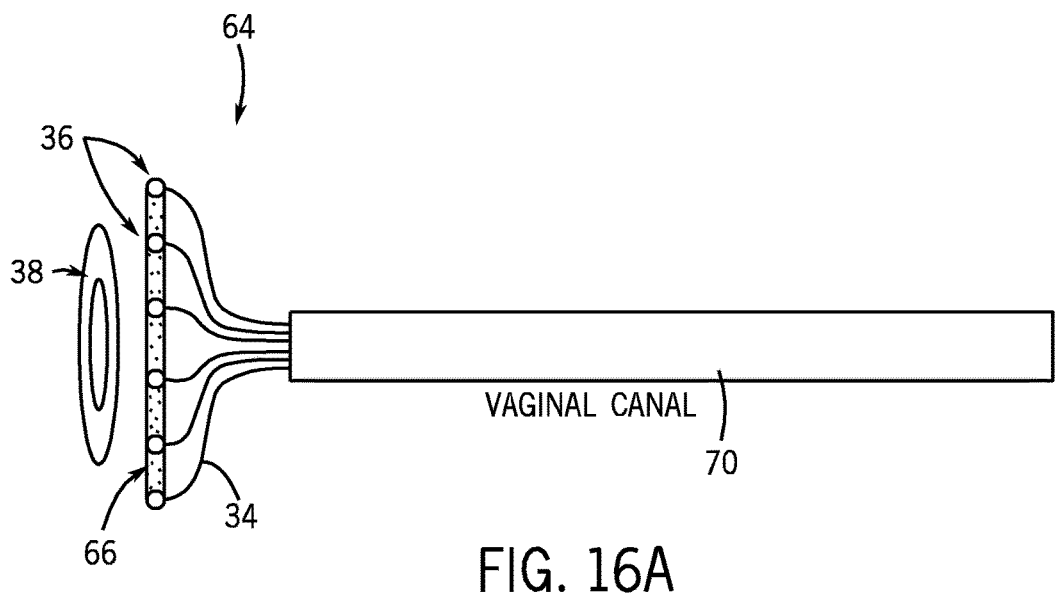
FIG. 16A is a side views of the ring electrode array device of FIG. 15A, including applicators.
Figure 16B:
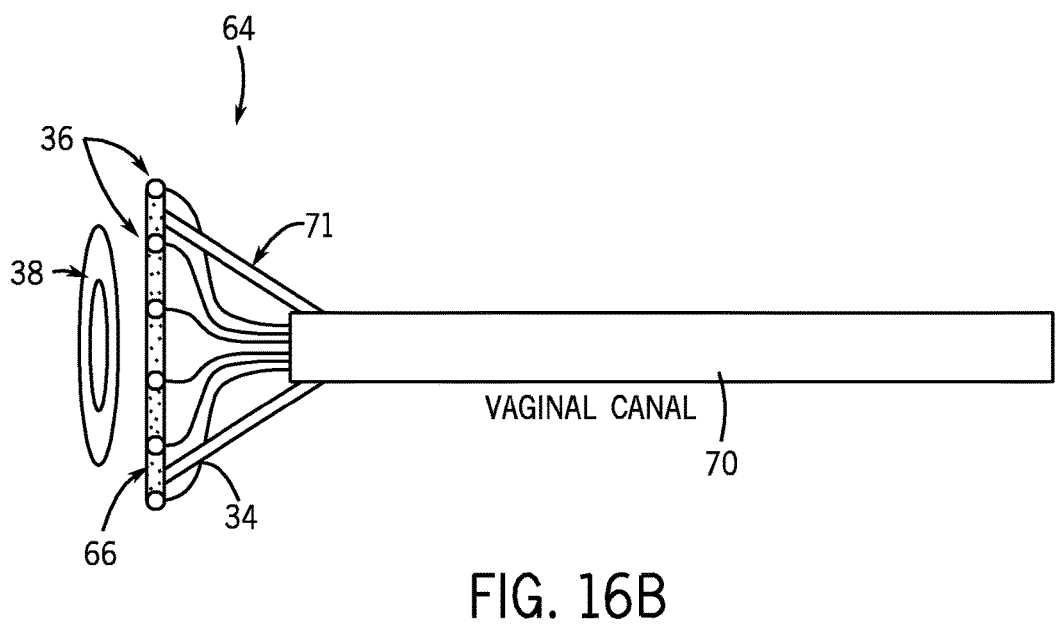
FIG. 16B is a side view of the ring electrode array device of FIG. 15A, including applicators.

In other embodiments, some or all of the lead wires 34 can be bundled into an applicator 70, as shown in FIGS. 16A and 16B, and coupled to the system 22 (either directly or via the lead cable connector 68). The applicator 70 can be a rigid or semi-rigid cylindrical probe (made of metal, rigid plastic, etc.) and, in some embodiments, can be coupled to the ring 66. The applicator 70 can be permanently coupled to the ring 66 (e.g., by an affixing structure 71, as shown in FIG. 16B) or can be detached from the ring 66 and removable. In addition, in one embodiment, the ring 66 can be collapsed into the applicator 70 or around an outside portion of the applicator 70. For example, the ring can be collapsed into the applicator 70 and the lead wires 34 can be bundled into the applicator 70 for ease of insertion trans-vaginally. If the applicator 70 is not used, the ring 66 can be inserted manually by hand, for example by first collapsing the ring 66 manually.

The ring 66 can be positioned in the vaginal canal against the cervix 46 or fornix during application of electrical stimulation (i.e., using stimulation frequencies greater than or equal to about 5 Hz) in order to allow electrical current to flow between adjacent electrodes 36, and indirectly through the uterus 38 and/or through the uterine artery, thus initiating contractile activity of the uterus 38 or arteries sufficient to reduce bleeding (e.g., during uterine atony or postpartum hemorrhage). If the applicator 70 is permanently coupled to the ring 66, as shown in FIG. 16B, it can remain within the vaginal canal during electrical stimulation of the electrodes 36. If the applicator 70 is detachable from the ring 66, as shown in FIG. 16A, it can be removed prior to electrical stimulation, if desired. In some embodiments, the device 64, including the applicator 70, can be disposable. In other embodiments, at least some components of the device 64, such as the applicator 70, can be sterilizable for multiple uses.

In addition, the ring electrode array device 64 can be capable of delivering medication (i.e., via absorption) to the uterus 38 or surrounding tissue, simultaneous to the uterine electrical stimulation. The medication can be impregnated into and gradually released from the ring 66.

Figure 17A:
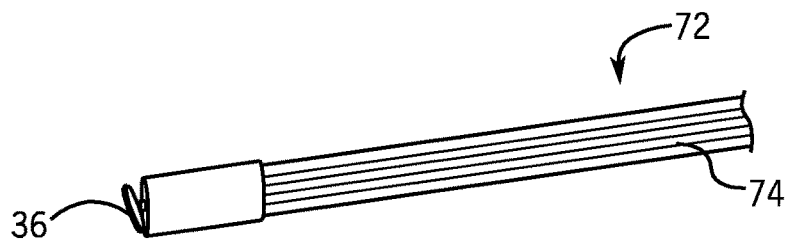
FIG. 17A is a perspective views of an electrode probe device for use with the present invention.
Figure 17B:
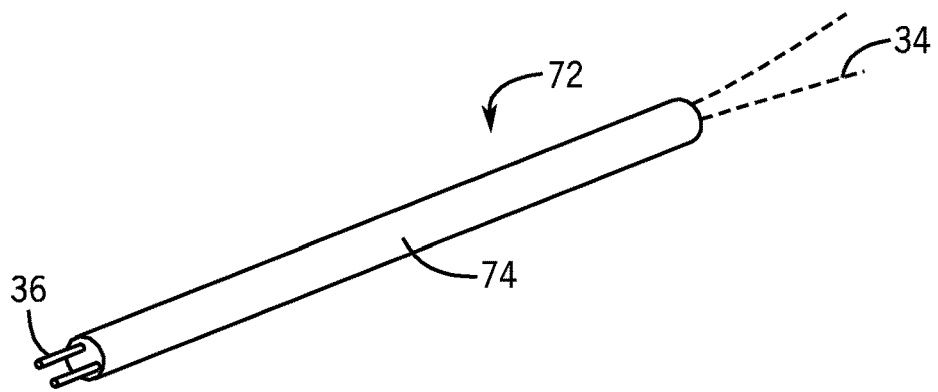
FIG. 17B is a perspective views of an electrode probe device for use with the present invention.
Figure 17C:
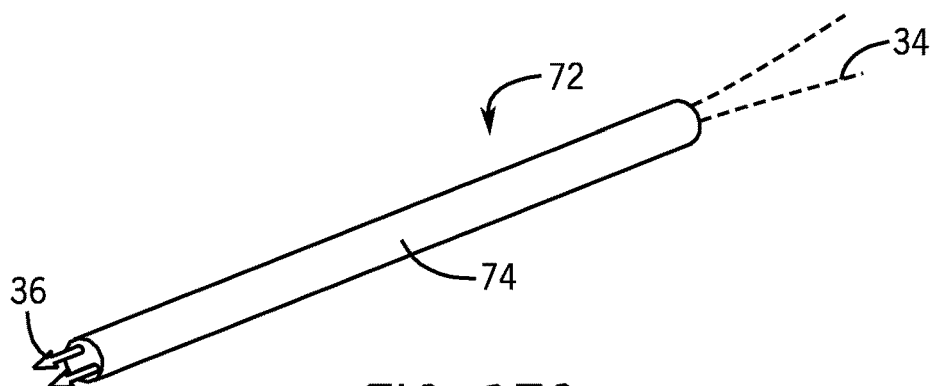
FIG. 17C are perspective views of an electrode probe device for use with the present invention.

In some embodiments, the system 22 can include an electrode probe device 72, as shown in FIGS. 17A-17C. The electrode probe device 72 can be a rigid or semi-rigid cylindrical probe 74, outfitted with the electrodes 36 at one end and the connecting lead wires 34 within the probe 74 extending out at another end and inserted trans-vaginally for assisting with reducing blood flow from the uterus 38 during postpartum hemorrhage through electrical stimulation (i.e., using stimulation frequencies greater than or equal to about 5 Hz for inducing tonic or tetanic contractions). Also, in some embodiments, the electrode probe device 72 can be used to assist with inducing contractions in laboring women (i.e., using conventional stimulation frequencies for inducing stimulated phasic contractions).

The electrode probe device 72 can include a probe 74 comprising rubber, latex, Tygon®, metal, plastic, or a similar material, generally in the shape of a hollow or substantially solid cylinder. The electrode probe device 72 can include electrodes 36 affixed to an outer surface end of the probe 74. The electrodes 36 can be embedded within or incorporated into the probe 74 so that the electrodes 36 are exposed at the outer surface end of the probe 74. In addition, the electrode probe device 72 can include insulated lead wires 34 for transmitting electrical current to the electrodes 36. The lead wires 34 can be partially coupled to or embedded in the probe 74. For example, the lead wires 34 can be routed through a hollow tube within the probe 74 so that one end of each lead wire 34 is attached to an electrode 36 and another end of each lead wire 34 is coupled to an electrical lead cable (e.g., similar to the lead cable connector 68, as shown in FIG. 15A, connected to the system 22). In addition, all or at least some of the lead wires 34 can be bundled together and routed through a hollow tube within the probe 74.

The electrode probe device 72 can be positioned through the vaginal canal so that the electrodes 36 are positioned against or into the tissues of the cervix or fornix, or through the cervix 46 into the uterine cavity and positioned directly against or into the inner uterine wall. Application of electrical stimulation (i.e., using stimulation frequencies greater than or equal to about 5 Hz) can allow electrical current to flow between adjacent electrodes 36, and thus flow indirectly or directly through the uterus and/or through the uterine artery, thus initiating contractile activity of the uterus or arteries sufficient to reduce bleeding (e.g., during uterine atony or postpartum hemorrhage).

In some embodiments, the entire device 72 can be disposable. In other embodiments, at least some components of the device 72 can be sterilizable for multiple uses. In one embodiment, as shown in FIG. 17A, the probe 74 can include a single spiral electrode 34 protruding from one end, and lead wires 34 routed through a hollow portion of the probe 74. In another embodiment, as shown in FIG. 17B, the probe 74 can include one or more "bar" or "rod" electrodes 36 protruding from one end. In yet another embodiment, as shown in FIG. 17C, the probe 74 can include one or more "barb" or "needle" electrodes 36 protruding from one end. In some embodiments, multiple probes 74 can be used simultaneously, as needed, to apply sufficient electrical current in a sufficient number of locations on the uterus, cervix, or fornix in order to produce an adequate uterine contractile response.

In addition, the electrode probe device 72 can be capable of delivering medication (i.e., via injection) to the uterus 38 or surrounding tissue, simultaneous to the uterine electrical stimulation.

In some embodiments, the system 22 can include a mesh electrode array device 76, as shown in FIGS. 18A-20C. The mesh electrode array device 76 can comprise an array of electrodes 36 in the form of a "net," "web," or "mesh" 78 of electrically non-conductive, flexible, and/or stretchable material supporting the conductive electrode elements 36 and/or conductive lead wires 34. The mesh electrode array device 76 can be inserted trans-vaginally for assisting with reducing blood flow from the uterus 38 during postpartum hemorrhage through electrical stimulation (i.e., using stimulation frequencies greater than or equal to about 5 Hz for inducing tonic or tetanic contractions). Also, in some embodiments, the mesh electrode array device 76 can be used to assist with inducing contractions in laboring women (i.e., using conventional stimulation frequencies for inducing stimulated phasic contractions).

Figure 18A:
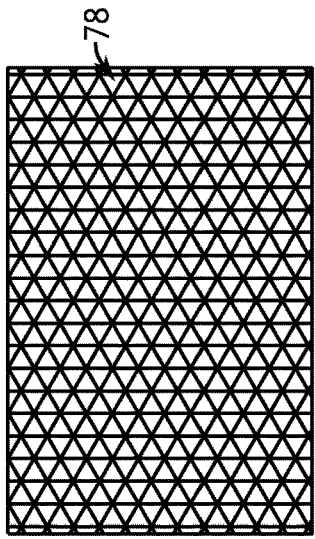
FIG. 18A is a mesh structures of a mesh electrode array device for use with the present invention.
Figure 18B:
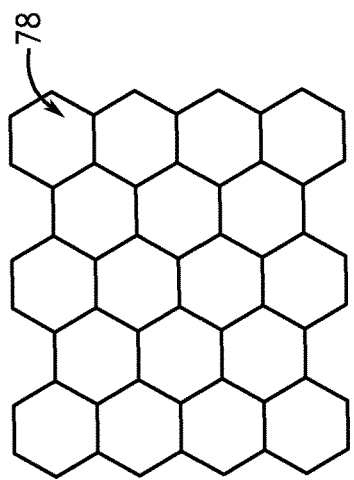
FIG. 18B is a mesh structures of a mesh electrode array device for use with the present invention.

The non-conductive mesh material 78 can provide a framework to non-conductively connect or link each electrode 36 to one or more other electrodes 36. The non-conductive mesh material 78 can be a supporting substrate having one or more segments constructed of flat, rounded, cylindrical, and/or other-shaped material. In some embodiments, the non-conductive mesh material 78 can comprise silicone, latex, rubber, plastic, nylon, etc., so that the device 76 can stretch and twist effectively in multiple directions. In addition, the non-conductive mesh material 78 can be fabricated to include a constant or variable framework or base structure, including square, hexagonal, triangular, and/or other mesh shapes, as shown in FIGS. 18A and 18B.

The mesh electrode array device 76 can expand (e.g., substantially open up, unfold, stretch out, etc.) to a size sufficient to cover, envelope, or encircle the uterus 38. The device 76 can expand into a general sphere, general ovoid, or general cigar shape, having dimensions between about 5 centimeters major or minor diameter up to about 50 centimeters major or minor diameter. For example, in one embodiment, the device 76 can be fabricated to form-fit snugly around the entire outer surface of a uterus 38 before and/or after delivery of the fetus by cesarean-section. In addition, the non-conductive mesh material 78 can include gaps, slits, or other openings positioned therein in order to accommodate uterine arteries and various ligaments when deployed onto the uterus 38. The device 76 can also be specifically fabricated in various sizes in order to accommodate, as appropriate, either a small, medium, or large size uterus 38.

Figure 19:
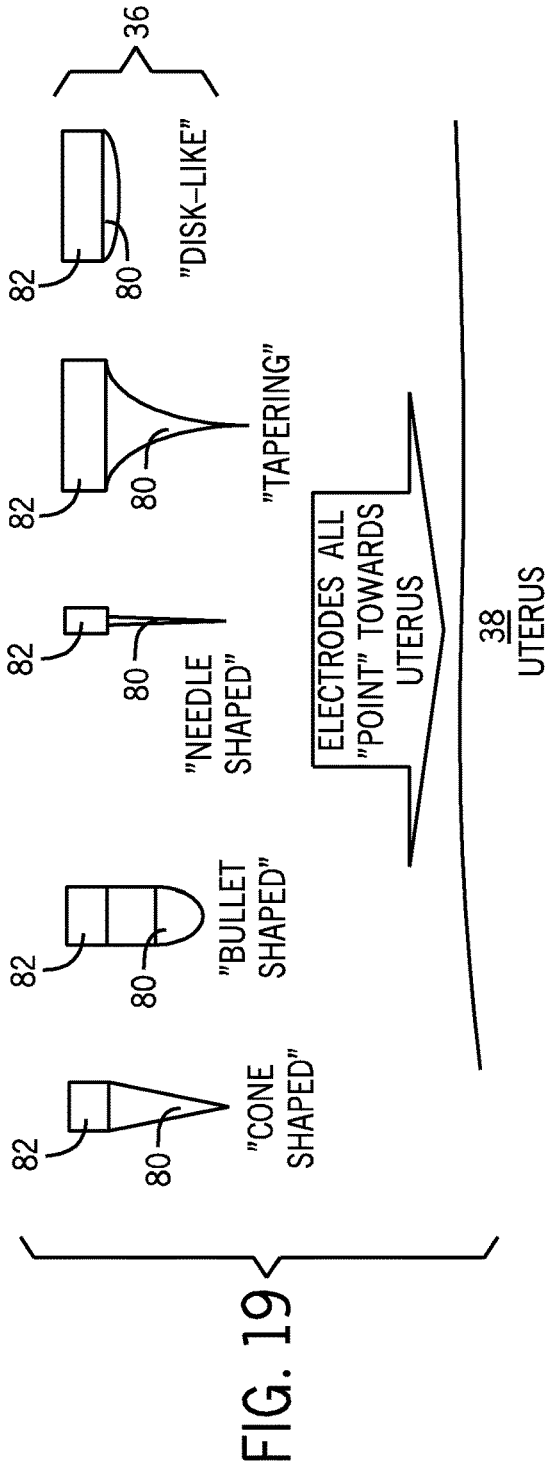
FIG. 19 illustrates side views of electrodes for use with the present invention.

The electrodes 36 can be positioned along and within the non-conductive mesh material 78 at nodes of intersection of the strands or segments and/or along the length of the strands or segments. The electrodes 36 can include materials which are electrically conductive, such as metal, graphite, ceramic, polymer, or other rigid or semi-rigid and conductive substances. In some embodiments, as shown in FIG. 19, each electrode 36 can include a tip 80 and a housing 82 coupled together mechanically or chemically. The tip 80 (e.g., a conductive portion) can be connected to or positioned on the uterine tissue for passing electrical current thereto, and the housing 82 (e.g., an electrically non-conductive portion) can be coupled to the non-conductive mesh material 78. The housings 82 can include a rigid or semi-rigid electrically non-conductive material, such as plastic, rubber, polymer, etc., and can include passages, gaps, grooves, and/or ridges through which or into which the lead wires 34 can pass to electrically connect with the tips 80. As shown in FIG. 19, the electrodes 36 can include one or more shapes, such as needles, spikes, point, nubs, grommets, nipples, disks, or any other form, feature, or shape to provide sufficient electrical conductivity and connectivity between the electrodes 36 and the uterine tissue, and to transmit electrical current to/from the electrodes 36 and uterine tissue. The above-described shapes of electrodes 36 can be incorporated into one or more of the devices 54, 64, 72, 76 in some embodiments.

The mesh electrode array device 76 can include sufficient tensile strength and elastic force so that a physician can fully and manually deploy it around and onto the uterus 38 with relative ease by hand with minimal risk of injury to the patient and to the physician during handling and deployment. In addition, the electrodes 36 can be oriented in such a way within and on the non-conductive mesh material 78 so that the tips 80 are directed toward the uterine tissue when the device 76 is deployed (e.g., placed onto and expanded around the outer surface of the uterus 38, for example during cesarean section). More specifically, the mesh electrode array device 76 can include sufficient tensile strength and elastic force so that when the device 76 is deployed, the electrodes 36 will rest firmly against the outer surface of the uterus 38, or so that portions of the electrodes 36 will penetrate through an outer membrane of the outer surface of the uterus 38 (e.g., when using needle-shaped or other pointed-tip types of electrodes 36).

In some embodiments, the mesh electrode array device 76 can include pairs of electrodes 36 (e.g., each pair including a positive electrode and a negative electrode), with each pair of electrodes 36 capable of transmitting an individual, distinct electrical current through the uterine tissue. The electrodes can receive electrical stimulation current (e.g., can be electrically activated by and fed electrical stimulation current from the system 22) via two or more lead wires 34 (e.g., at least one positive lead wire 34 and at least one negative lead wire 34).

Figure 20A:
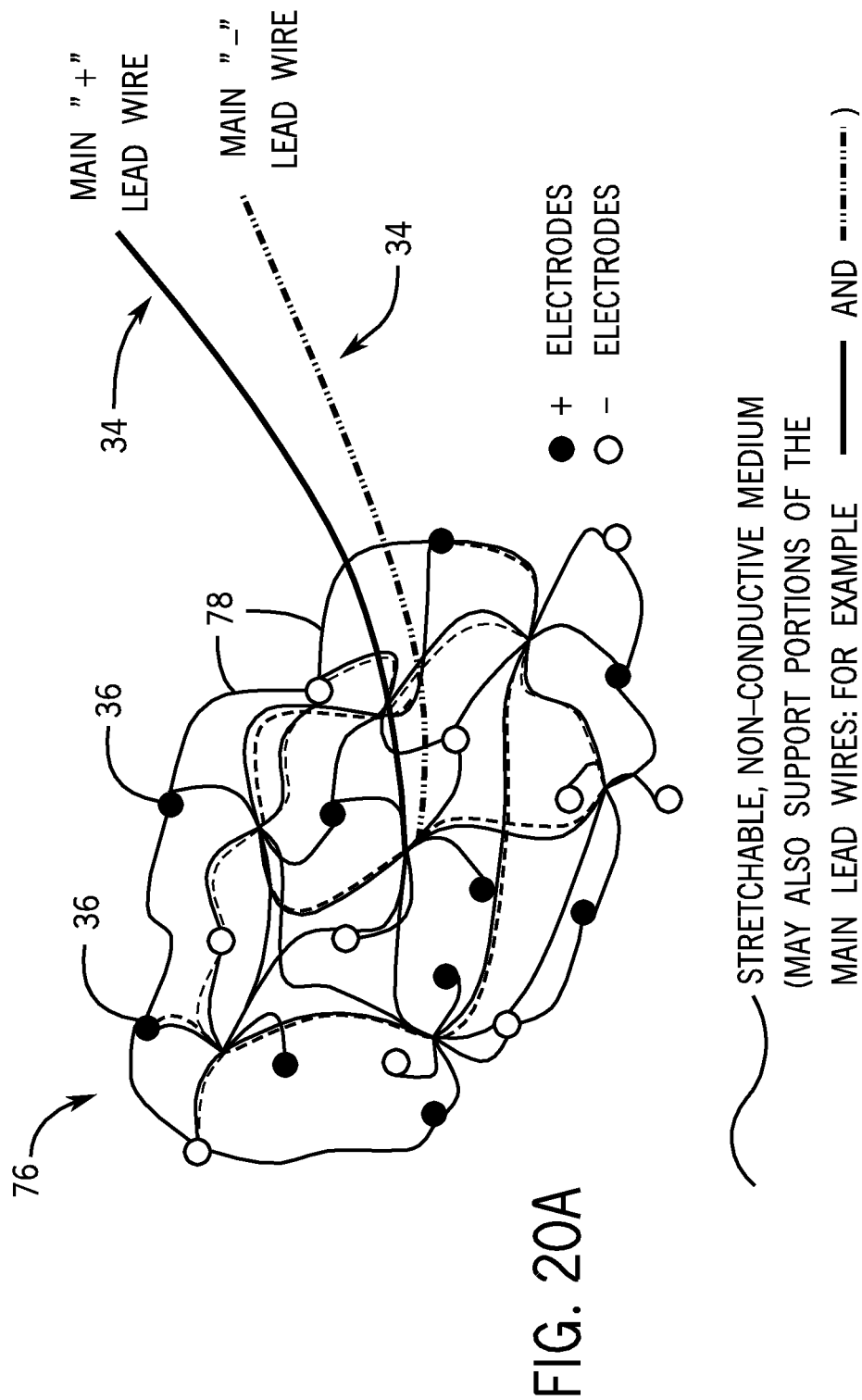
FIG. 20A is a perspective views of a mesh electrode array device for use with the present invention.
Figure 20B:
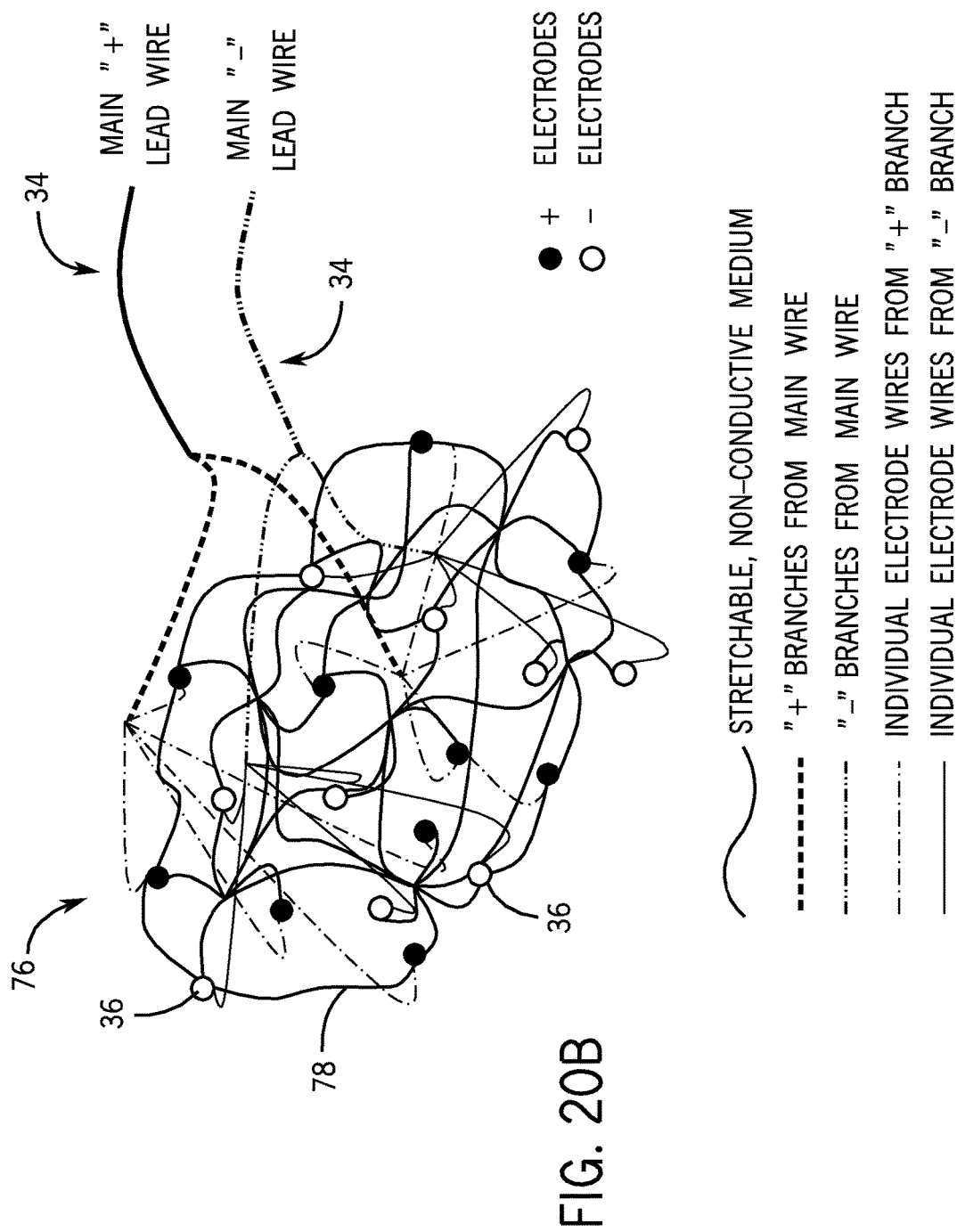
FIG. 20B is a perspective views of a mesh electrode array device for use with the present invention.
Figure 20C:
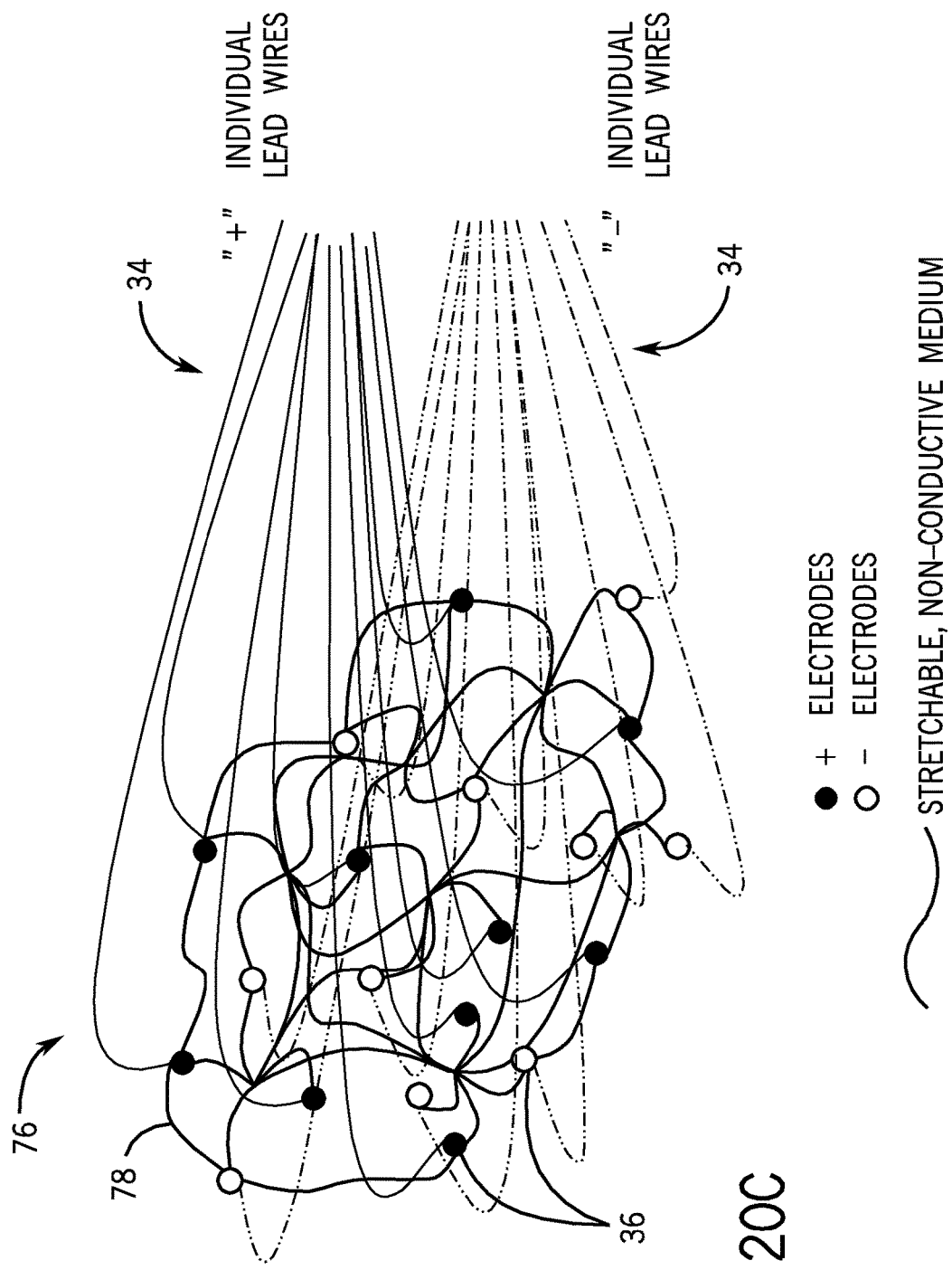
FIG. 20C is a perspective views of a mesh electrode array device for use with the present invention.

For example, the designated positive electrodes 36 (e.g., from the electrode pairs) can receive electrical stimulation current from a single main positive voltage lead wire 34, and the designated negative electrodes 36 can receive electrical stimulation current from a single main negative voltage lead wire 34, as shown in FIG. 20A. In another example, the designated positive electrodes 36 can receive electrical stimulation current from different positive voltage lead wires 34, which are branched off from the single main positive voltage lead wire 34, and the designated negative electrodes 36 can receive electrical stimulation current from different negative voltage lead wires 34, which are branched off from the single main negative voltage lead wire 34, as shown in FIG. 20B. In yet another example, the designated positive electrodes 36 can receive electrical stimulation current from separate, individual positive voltage lead wires 34, and the designated negative electrodes 36 can receive electrical stimulation current from separate, individual negative voltage lead wires 34, as shown in FIG. 20C.

In some embodiments, at least some portions of the electrodes 36 (e.g., the tips 80 or other portions) of the above-described devices 54, 64, 72, 76, can be fitted with, covered by, coated with, or impregnated with conductive epoxy, medication, friction-reducing compounds, or other substances for improving the electrical conductivity between the electrode 36 and the uterine tissue, for treating the patient or the uterus, for improving the effect of electrical stimulation of the uterus 38, for improving uterine contractility, and/or for enhancing the ease with which electrodes 36 are applied to or into the uterine tissue. In addition, at least some portions of the electrodes 36 (e.g., the tips 80 or other portions) can be fitted with, covered by, coated with, or impregnated with insulating epoxy, friction-reducing compounds, or other substances (e.g., polytetrafluoroethylene, or PTFE, resin) for eliminating or reducing electrical conductivity and contact between such portions of the electrodes 36 and the uterine tissue.

In addition, in some embodiments, the electrodes 36 of the above-described devices 54, 64, 72, 76 can be temporarily covered by tabs, covers, or safety guards (not shown) for protecting the patient and user from punctures or cuts during handling prior to or during deployment of the devices 54, 64, 72, 76. The safety guards can individually be removed manually upon, after, or prior to deploying the device, and can be replaced, if desired.

In some embodiments, the above-described devices 54, 64, 72, 76 or other external, internal, or transvaginally, transcervically, percutaneously, or transabdomoinally placed needles, catheters, probes, electrodes or electrode arrays may be outfitted with the cable connector 68 or a similar device in order to be coupled to the system 22 for receiving electrical stimulation current (e.g., from the biphasic converter 32) via a connector and cable device 84, as shown in FIGS. 21A-23B. The device 84 can include a lead wire connector plug 86, an electronics connector plug 88, and a flexible, electrically insulated cable 90.

In one embodiment, the electronics connector plug 88 can connect to the biphasic converter 32 for receiving electrical stimulation current. In another embodiment, components of the system 22 (e.g., the control module 24, the current source 26, the isolation unit 28, the constant maximum current unit 30, the biphasic converter 32) can be housed in a single electronics box (not shown) and the electronics connector plug 88 can be connected to the electronics box for receiving electrical stimulation current. The electrical stimulation current can be routed from the electronics connector plug 88 to the lead wire connector plug 86 via the cable 90. In some embodiments, the plugs 86 and 88, and the cable 90 can be permanently coupled as a single unit. In other embodiments, the plugs 86 and 88, and the cable 90 can be releasably coupled together, for example so that some portions can be disposable and some portions can be sterilizable (e.g., using radiation, gas, and/or heat).

Figure 21A:
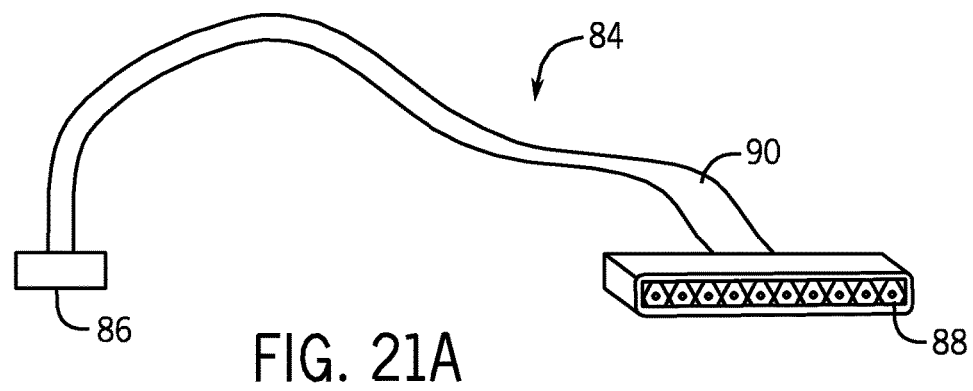
FIG. 21A is a perspective view of a connector and cable device for use with the present invention.
Figure 21B:
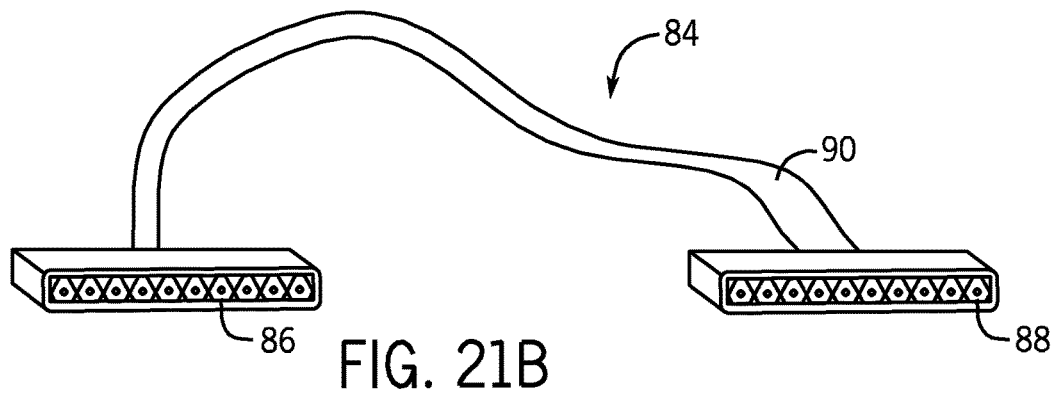
FIG. 21B is a perspective view of another connector and cable device for use with the present invention.

In some embodiments, the lead wire connector plug 86 and/or the electronics connector plug 88 can comprise conventional connector plugs, such as DIN connectors, BNC connectors, coaxial connectors, banana connectors, LEMO connectors, etc., for connecting to the lead wires 34 and/or the electronics box, respectively. In some embodiments, the lead wire connector plug 86 and/or the electronics connector plug 88 can comprise a pin connector array, as described below. For example, FIG. 21A illustrates the lead wire connector plug 86 and the electronics connector plug 88 as a generic connector and a pin connector array, respectively. FIG. 21B illustrates both the lead wire connector plug 86 and the electronics connector plug 88 as pin connector arrays.

Figure 22A:
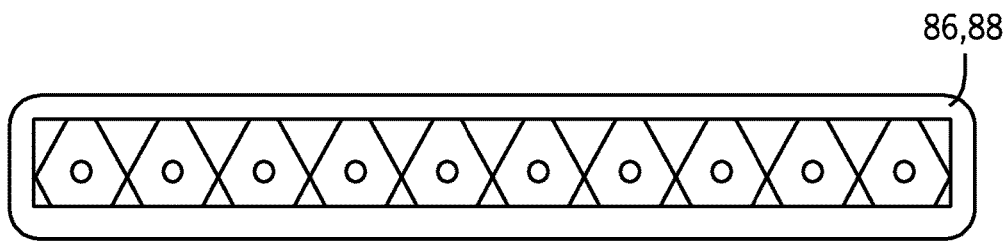
FIG. 22A is a front views of pin connector arrays of the connector and cable device of FIGS. 21A and 21B.
Figure 22B:
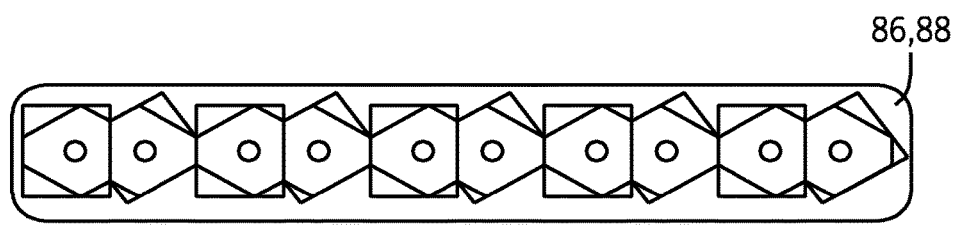
FIG. 22B is a front views of pin connector arrays of the connector and cable device of FIGS. 21A and 21B.
Figure 23A:
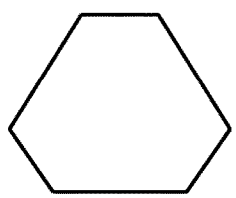
FIG. 23A is a schematic views of a connector pin of the pin connector arrays of FIGS. 22A and 22B.
Figure 23B:
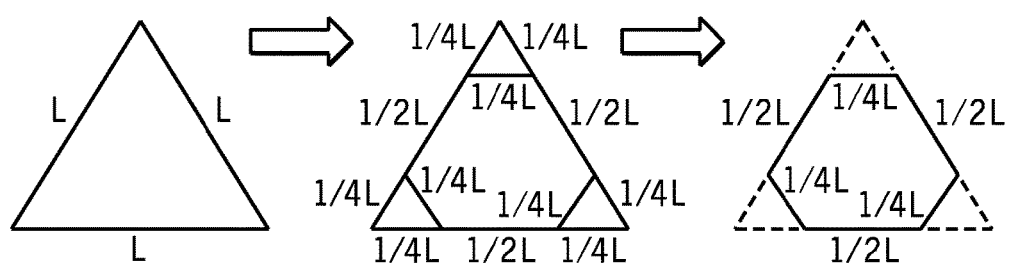
FIG. 23B is a schematic views of a connector pin of the pin connector arrays of FIGS. 22A and 22B.

The pin connector array can include a plurality of pin connectors, as shown in FIGS. 22A and 22B. In one embodiment, each pin connector can comprise an irregular, symmetric hexagonal shape, as shown in FIG. 23A. For example, the hexagonal shape can take the form of an equilateral triangle of length L, with wedges (length ¼L) at each vertex of the equilateral triangle removed, as shown in FIG. 23B. In other embodiments, the pin connectors can comprise other shapes.

The pin connectors can be positioned relative to each other on the pin connector array in one or more arrangements, as shown in FIGS. 22A and 22B. For example, the "flip flop" arrangement illustrated in FIG. 22B can be substantially shorter than the "in-line" arrangement illustrated in FIG. 22A. In addition, FIGS. 22A and 22B show 10 pin connectors in each pin connector array. In some embodiments, the pin connector arrays can include one to fifty or more pin connectors.

Figure 24A:
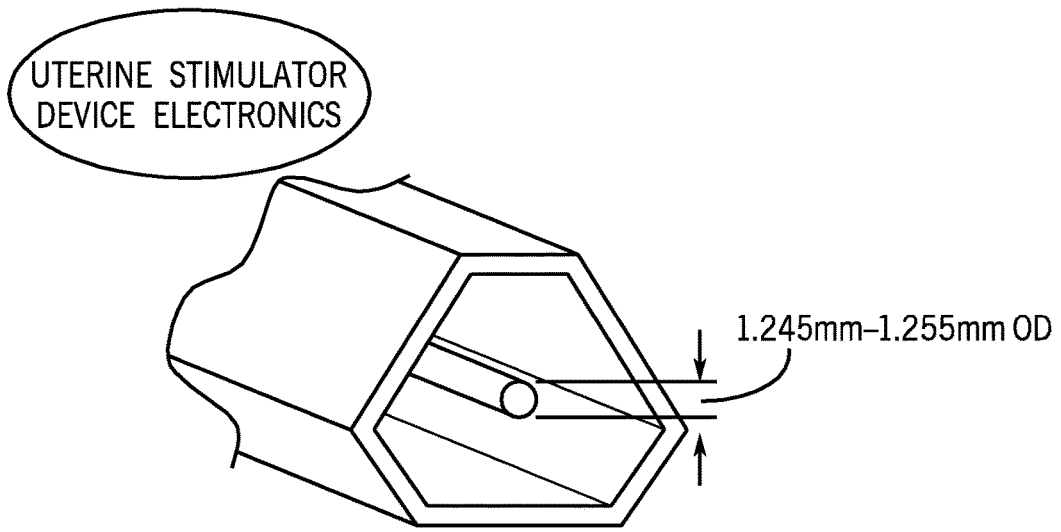
FIG. 24A is a perspective view of a male connector pin for use with the pin connector arrays of FIGS. 22A and 22B.
Figure 24B:
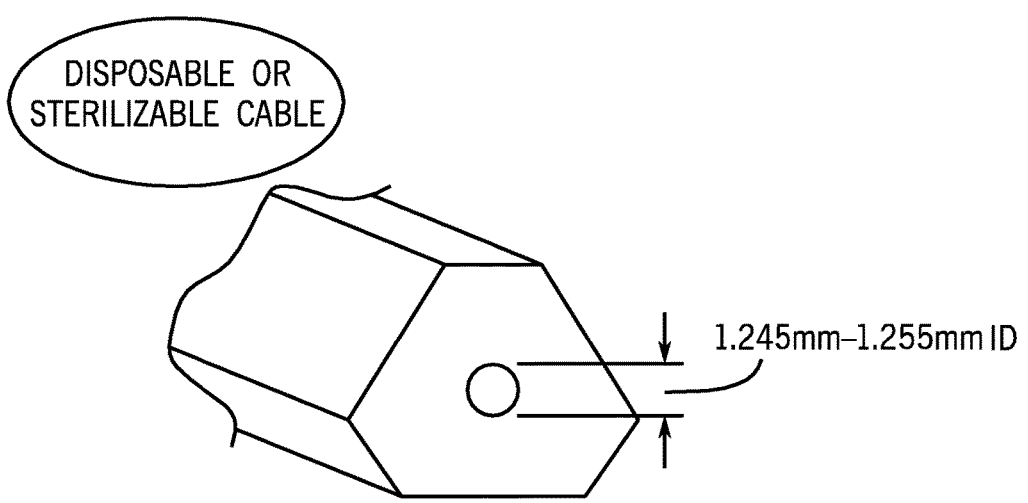
FIG. 24B is a perspective view of a female connector pin for use with the pin connector arrays of FIGS. 22A and 22B.

In one embodiment, the electronics box and/or the lead wires 34 can include corresponding male connectors for receiving the pin connectors (e.g., female connectors) of the plugs 86, 88. In another embodiment, the electronics box and/or the lead wires 34 can include corresponding female connectors for receiving the pin connectors (e.g., male connectors) of the plugs 86, 88. In either embodiment, the male connectors can include a cylindrical pin protruding from the general center of the hexagonal shaped connector, as shown in FIG. 24A. The pin can include an outside diameter between about 1.245 millimeters and about 1.255 millimeters in some embodiments. The female connectors can include mating cylindrical holes for the cylindrical pins of the male connectors, as shown in FIG. 24B. The holes can include an inner diameter between about 1.245 millimeters and about 1.255 millimeters in some embodiments. In addition, the pin connectors can be plastic, while the protruding pins can be metallic and the holes can include metallic internal sleeves. The pins and internal sleeves can also comprise other conductive materials in some embodiments. In addition, the pin connector arrays or the individual pin connectors can include one or more locking mechanisms. In one embodiment, the locking mechanism, either on the plastic or the conductive portions of the pin connectors, can substantially lock the pin connector arrays in place when the female connectors and the male connectors are connected. Once connected, the female connectors and the male connectors can be broken or disabled when separated, ensuring one-time use of the pin connector arrays.

In some embodiments, the cable 90 can include a plurality of electrically conductive materials or wires (e.g., metal, carbon-based elements, etc.). The electrically conductive wires can be substantially flexible and bunched, threaded, braided, or twisted through the cable 90. The electrically conductive wires can be electrically insulated externally by materials such as plastic, rubber, silicone, or other non-conductive media. Each hole in the pin connector array (of the female connectors) at the plug 86 can be associated with a separate electrically conductive wire, which can be connected to an associated pin or sleeve (of the male connectors or the female connectors, respectively) at the plug 88.

In some embodiments, the connector and cable device 84 can include electrical circuitry, computer software or hardware, logic circuits, instructions, codes, and/or programs stored in memory and executable by the electrical circuitry, which can serve one or more of following functions: measuring or communicating electrical impedance values (in the patient, between electrodes 36, and/or between the patient and electrodes 36); determining or communicating the electrical or physical integrity of the cable 90, the plugs 86, 88, and/or any of the electrodes 36; communicating an embedded serial code, license code, model number, or other electronically stored or coded information about the connector and cable device 84 to the electronics in the system 22; and preventing the operation of providing electrical stimulation current if cable or plug portions become detached, separated, broken, compromised, or otherwise altered, or if the serial code is not correct or identifiable by the system 22.

The present invention has been described in terms of one or more preferred embodiments, and it should be appreciated that many equivalents, alternatives, variations, and modifications, aside from those expressly stated, are possible and within the scope of the invention.

The entire disclosure of each patent and publication cited herein is incorporated by reference, as if each such patent or publication were individually incorporated by reference herein. Unless defined otherwise, technical and scientific terms used herein have the same meaning as commonly understood by one of ordinary skill in the art to which this invention belongs. Singleton et al., Dictionary of Microbiology and Molecular Biology 3rd ed., J. Wiley & Sons (New York, N.Y. 2001); March, Advanced Organic Chemistry Reactions, Mechanisms and Structure 5th ed., J. Wiley & Sons (New York, N.Y. 2001), and Sambrook and Russel, Molecular Cloning: A Laboratory Manual 3rd ed., Cold Spring Harbor Laboratory Press (Cold Spring Harbor, N.Y. 2001), provide one skilled in the art with a general guide to many of the terms used in the present application.

REFERENCES

1. The Prevention and Management of Postpartum Haemorrhage: Report of Technical Working Group, Geneva 3-6 Jul. 1989. Geneva: World Health Organization, 1990.

2. Elboume D R, Prendiville W J, Carroli G, Wood J, McDonald S. Prophylactic use of oxytocin in the third stage of labour. Cochrane Database Syst Rev 2001; (4): CD001808.

3. Bais J M, Eskes M, Pel M, Bonsel G J, Bieker O P. Postpartum haemorrhage in nulliparous women: incidence and risk factors in low and high risk women. A Dutch population-based cohort study on standard (>=500 mL) and severe (>=1000 mL) postpartum haemorrhage. Eur J Obstet Gynecol Reprod Biol 2004; 115:166-72.

4. Reyal F, Deffarges J, Luton D, Blot P, Oury J F, Sibony O. Severe post-partum hemorrhage: descriptive study at the Robert-Debre Hospital maternity ward [French]. J Gynecol Obstet Biol Reprod (Paris) 2002; 31:358-64.

5. Norris T C. Management of postpartum hemorrhage. Am Fam Physician. 1997 Feb. 1; 55(2):635-40.

6. Fawcus, S, Mbizvo, M, Lindmark, G, Nystrom, L. A community-based investigation of maternal mortality from obstetric haemorrhage in rural Zimbabwe. Maternal Mortality Study Group. Trop Doct. 1997 July; 27(3):159-63.

7. Sultatos L G. Mechanisms of drugs that affect uterine motility. J Nurse Midwifery. 1997 July-August; 42(4):367-70.

8. Alexander E. Weingarten, M D, Jeffrey I. Korsh, M D, George G. Neuman, M D, and Steven B. Stem, M D. Postpartum Uterine Atony after Intravenous Dantrolene. Anesth Analg 1987; 66:269-270.

9. Hacker, Neville, J. G. Moore, and Joseph Gambone. Essentials of Obstetrics and Gynecology. 4th ed. Vol. 1. Philadelphia: Elsevier Inc., 2004. 151.

10. Bennie S D, Petrofsky J S, Nisperos J, Tsurudome M, Laymon M. Eur J Appl Physiol. 2002 November; 88(1-2): 13-9. Epub 2002 Sep. 10. Toward the optimal waveform for electrical stimulation of human muscle.

11. DeLisa, Joel A.; Gans, Bruce M.; Walsh, Nicolas E.; Bockenek, William L.; Frontera, Walter R.; Gerber, Lynn H.; Geiringer, Steve R.; Pease, William S.; Robinson, Lawrence R.; Smith, Jay; Stitik, Todd P.; Zafonte, Ross D. Physical Medicine and Rehabilitation: Principles and Practice. 4th edition. 2004. Lippincott Williams & Wilkins (LWW): Chapter 66.

12. Piallat B, Chabardes S, Devergnas A, Torres N, Allain M, Barrat E, Benabid A L. Monophasic but not biphasic pulses induce brain tissue damage during monopolar high-frequency deep brain stimulation. Neurosurgery. 2009 January; 64(1):156-62, discussion 162-3.

The invention claimed is:

1. A device configured to apply stimulating current to a patient for treating insufficient uterine contractions, the device comprising:
    an applicator with a first end and an opposite second end and sized to extend through a vaginal canal;
    at least one electrode positioned adjacent to the first end and configured to be arranged proximate to at least one of a cervix or a fornix of the patient; and
    at least one lead wire that is electrically coupled to the at least one electrode and is routed through the applicator so that it exits the applicator adjacent to the second end to deliver electrical current through the applicator to the at least one electrode to initiate contractile activity of a uterus of the patient when the applicator is extended through the vaginal canal to engage the at least one electrode proximate to at least one of the cervix or the fornix of the patient,
    wherein the at least one electrode forms an array device comprising:
        a flexible ring, and
        a plurality of electrodes affixed to an outer surface of the flexible ring, and
        the at least one lead wire comprises a plurality of lead wires electrically coupled to the plurality of electrodes.

2. The device as recited in claim 1 wherein the applicator is constructed of one of rubber, latex, metal, and plastic.

3. The device as recited in claim 1 wherein the at least one electrode is coated with and used to administer a medication.

4. The device as recited in claim 1 wherein the applicator forms a cylindrical shape and, wherein the flexible ring is collapsible within the applicator to facilitate trans-vaginal insertion into the uterus of the patient.

5. The device as recited in claim 1 wherein at least one of the flexible ring and the plurality of electrodes is impregnated or coated with a medication.

6. The device as recited in claim 1, further comprising: a connector and cable device configured to connect a system that produces stimulating current with the at least one electrode to apply the stimulating current to the patient for treating insufficient uterine contractions.

7. The device as recited claim 6, wherein the connector device comprises: an electronics connector plug capable of being releasably coupled to the system and configured to receive the stimulating current from the system; and a lead wire connector plug releasably coupled between the at least one wire lead and the at least one electrode to deliver the stimulating current to the at least one electrode.

8. The device as recited in claim 7, wherein at least one of the electronics connector plug, the lead wire connector plug, and the at least one lead wire contains electrical circuitry and one of computer software, computer hardware, logic circuits, instructions, codes, and programs stored in memory and executable by the electrical circuitry.

9. The device as recited claim 8, wherein the programs cause one of the system that produces stimulating current or the electrical circuitry to carry out steps comprising: generating electrical stimulating current signals at a frequency between about 5.0 Hertz and about 100 Hertz; and applying the electrical stimulating current signals to one of a cervix, a vagina, an abdominal wall, and a uterus to produce uterine tonic contractions.

10. The device as recited in claim 1, further comprising: a control module which performs at least one of preprogrammed stimulation tasks and user-defined stimulation tasks; a current source controlled by the control module to produce stimulating current at a frequency between about 5.0 Hertz and about 100 Hertz; a connector configured to electrically couple the current source to the at least one lead wire to provide the stimulating current to the at least one electrode to produce tonic uterine contractions.

* * * * *